United States Patent
Grimanelli et al.

(10) Patent No.: US 9,234,209 B2
(45) Date of Patent: Jan. 12, 2016

(54) MEANS FOR INDUCING APOXIMIS IN CULTIVATED PLANTS HAVING SEXUAL REPRODUCTION AND USE THEREOF FOR THE PRODUCTION OF COMPLETELY OR PARTIALLY APOMICTIC PLANTS

(75) Inventors: Daniel Grimanelli, Assas (FR); Olivier Leblanc, Sainte Croix de Quintillargues (FR)

(73) Assignee: INSTITUT DE RECHERCHE POUR LE DEVELOPMENT (IRD), Marseille (FR)

(*) Notice: Subject to any disclaimer, the term of this patent is extended or adjusted under 35 U.S.C. 154(b) by 591 days.

(21) Appl. No.: 13/503,182

(22) PCT Filed: Oct. 21, 2010

(86) PCT No.: PCT/IB2010/054769
§ 371 (c)(1),
(2), (4) Date: Jul. 30, 2012

(87) PCT Pub. No.: WO2011/048566
PCT Pub. Date: Apr. 28, 2011

(65) Prior Publication Data
US 2012/0291155 A1 Nov. 15, 2012

(30) Foreign Application Priority Data
Oct. 21, 2009 (FR) .................................... 09 05046

(51) Int. Cl.
| C12N 15/82 | (2006.01) |
| C07K 14/415 | (2006.01) |
| A01H 1/06 | (2006.01) |
| A01H 5/00 | (2006.01) |
| A01H 5/10 | (2006.01) |
| C12N 15/113 | (2010.01) |

(52) U.S. Cl.
CPC .......... *C12N 15/8287* (2013.01); *C07K 14/415* (2013.01); *C12N 15/1137* (2013.01); *C12N 15/829* (2013.01)

(58) Field of Classification Search
None
See application file for complete search history.

(56) References Cited

U.S. PATENT DOCUMENTS

2003/0077623 A1* 4/2003 Butler et al. .................... 435/6
2005/0204427 A1 9/2005 Butler et al.

FOREIGN PATENT DOCUMENTS

WO   WO 97/11167   3/1997

OTHER PUBLICATIONS

Karen Bohmert et al. (1998). "AGO1 defines a novel locus of *Arabidosis* controlling leaf development." The EMBO Journal vol. 17 No. pp. 170-180.*
Ian Bancroft et al. (1991). "Development of an efficient two-element transposon tagging system in Arabidopsis thaliana" Mol Gen Genet vol. 227 pp. 391-396.*
Hunter et. al. (2003) "The Arabidopsis Heterochronic Gene ZIPPY Is an ARGONAUTE Family Member" Current Biology vol. 13 pp. 1734-1739.*
Nonomura et al. (2007) Plant Cell vol. 19 pp. 2583-2594.*
Vaucheret et. al., (2008) Trends in Plant Science vol. 13, pp. 350-358.*
Olmedo-Monfil et al (Mar. 25, 2010) Nature vol. 464, pp. 628-632.*
Bicknell et al (The Plant Cell (2004) vol. 16, pp. S228-S245.*
International Preliminary Report on Patentability dated May 8, 2012 and English translation of Written Opinion of the International Searching Authority issued in connection with PCT/IB2010/054769.
International Search Report for PCT/IB2010/054769, mailed Jan. 18, 2011.
Bicknell, R. A. et al., "Understanding apomixes: recent advances and remaining conundrums", The Plant Cell 2004, vol. 16 Suppl., (2004), pp. S228-S245.
Vaucheret et al., "Plant Argonautes", Trends in Plant Science, vol. 13, No. 7, (Jul. 1, 2008), pp. 350-358.
Olmedo-Monfil, V. et al., "Control of female gamete formation by a small RNA pathway in Arabidopsis", Nature, [Online] DOI: 10.1038/nature08828, (Mar. 7, 2010), 7 pages.

* cited by examiner

*Primary Examiner* — Amjad Abraham
*Assistant Examiner* — Ryan H Brown
(74) *Attorney, Agent, or Firm* — Young & Thompson

(57) ABSTRACT

The invention relates to the use of a gene of the Argonaute family, a transcript of said gene or the ORF of said gene in order to produce plants that are completely or partially apomictic. The invention can be used to control apomixis in cultivated species having sexual reproduction.

9 Claims, 5 Drawing Sheets

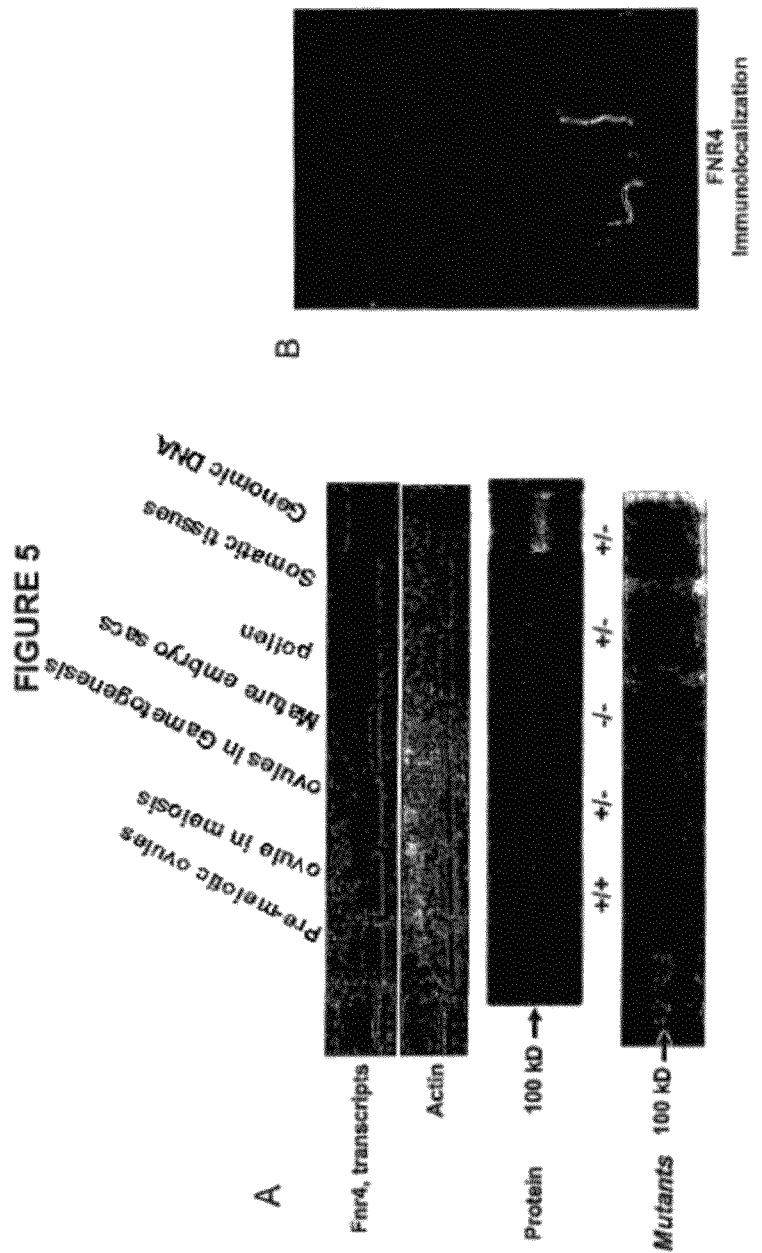

SEQUENCE LISTING

```
<160> NUMBER OF SEQ ID NOS: 9

<210> SEQ ID NO 1
<211> LENGTH: 910
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 1

| Met | Gly | Ser | His | Asp | Gly | Glu | Asp | Glu | Leu | Pro | Pro | Pro | Pro |
| 1 | | | | 5 | | | | | 10 | | | | 15 |

| Val | Pro | Pro | Asp | Val | Ile | Pro | Ile | Lys | Ala | Glu | Asp | Ala | Val | Gly | Glu |
| | | | 20 | | | | 25 | | | | | 30 | | | |

| Ser | Pro | Ala | Asn | His | Ile | Leu | Lys | Pro | Lys | Arg | Leu | Leu | Met | Asp | Arg |
| | | 35 | | | | | 40 | | | | | 45 | | | |

| Pro | Gly | Ile | Gly | Arg | Lys | Gly | Gln | Pro | Thr | Gln | Leu | Tyr | Ser | Asn | His |
| | 50 | | | | | 55 | | | | | 60 | | | | |

| Phe | Lys | Val | Ala | Val | Lys | Ser | Thr | Glu | Asp | Val | Phe | Phe | His | Tyr | Tyr |
| 65 | | | | | 70 | | | | | 75 | | | | | 80 |

| Val | Asn | Leu | Lys | Tyr | Glu | Asp | Asp | Arg | Pro | Val | Asp | Gly | Lys | Gly | Ile |
| | | | | 85 | | | | | 90 | | | | | 95 | |

| Gly | Arg | Lys | Val | Ile | Asp | Lys | Leu | Gln | Gln | Thr | Tyr | Arg | Ala | Glu | Leu |
| | | | 100 | | | | | 105 | | | | | 110 | | |

| Ser | Asn | Lys | Asp | Phe | Ala | Tyr | Asp | Gly | Glu | Lys | Ser | Leu | Phe | Thr | Val |
| | | 115 | | | | | 120 | | | | | 125 | | | |

| Gly | Gly | Leu | Pro | Gln | Lys | Lys | Asn | Glu | Phe | Thr | Val | Val | Leu | Glu | Asp |
| | 130 | | | | | 135 | | | | | 140 | | | | |

| Val | Ser | Thr | Gly | Lys | Thr | Ala | Ala | Asn | Gly | Ser | Pro | Gly | Gly | Asn | Asp |
| 145 | | | | | 150 | | | | | 155 | | | | | 160 |

| Ser | Pro | Gly | Gly | Gly | Asp | Arg | Lys | Arg | Val | Arg | Arg | Pro | Tyr | Gln | Thr |
| | | | | 165 | | | | | 170 | | | | | 175 | |

| Lys | Thr | Phe | Lys | Val | Glu | Ile | Asn | Phe | Ala | Ala | Glu | Val | Pro | Met | Ser |
| | | | 180 | | | | | 185 | | | | | 190 | | |

| Ala | Ile | Gly | Gln | Val | Ile | Arg | Gly | Glu | Glu | Ser | Glu | Asn | Ser | Leu | Glu |
| | | 195 | | | | | 200 | | | | | 205 | | | |

| Ala | Leu | Arg | Val | Leu | Asp | Ile | Ile | Leu | Arg | Gln | His | Ser | Ala | Glu | Gln |
| | 210 | | | | | 215 | | | | | 220 | | | | |

| Gly | Cys | Leu | Leu | Val | Lys | Gln | Ser | Phe | Phe | Tyr | Asn | Asn | Pro | Ser | Cys |
| 225 | | | | | 230 | | | | | 235 | | | | | 240 |

| Phe | Val | Asp | Leu | Gly | Gly | Gly | Val | Met | Gly | Cys | Arg | Gly | Phe | His | Ser |
| | | | | 245 | | | | | 250 | | | | | 255 | |

| Ser | Phe | Arg | Gly | Thr | Gln | Ser | Gly | Leu | Ser | Leu | Asn | Val | Asp | Val | Ser |
| | | | 260 | | | | | 265 | | | | | 270 | | |

| Thr | Thr | Met | Ile | Val | Lys | Pro | Gly | Pro | Val | Ile | Asp | Phe | Leu | Leu | Ser |
| | | 275 | | | | | 280 | | | | | 285 | | | |

| Asn | Gln | Asn | Val | Asn | Asp | Pro | Ser | Arg | Ile | Asp | Trp | Gln | Lys | Ala | Lys |
| | 290 | | | | | 295 | | | | | 300 | | | | |

| Arg | Ala | Leu | Lys | Gly | Leu | Arg | Ile | Arg | Thr | Thr | Pro | Ala | Asn | Ser | Glu |
| 305 | | | | | 310 | | | | | 315 | | | | | 320 |

| Phe | Lys | Ile | Phe | Gly | Leu | Ser | Glu | Arg | Ile | Cys | Lys | Glu | Gln | Thr | Phe |
| | | | | 325 | | | | | 330 | | | | | 335 | |

| Pro | Leu | Arg | Gln | Arg | Asn | Gly | Ser | Asn | Gly | Asp | Cys | Asp | Thr | Ile | Glu |
| | | | 340 | | | | | 345 | | | | | 350 | | |

| Ile | Thr | Val | Tyr | Asp | Tyr | Tyr | Ala | Lys | Lys | Gly | Ile | Asp | Leu | Lys | Tyr |
| | | 355 | | | | | 360 | | | | | 365 | | | |

| Ser | Gly | Asp | Phe | Pro | Cys | Ile | Asn | Thr | Gly | Lys | Ala | Lys | Arg | Pro | Thr |
| | 370 | | | | | 375 | | | | | 380 | | | | |

| Tyr | Phe | Pro | Ile | Glu | Leu | Cys | Ser | Leu | Val | Pro | Leu | Gln | Arg | Tyr | Thr |
| 385 | | | | | 390 | | | | | 395 | | | | | 400 |

| Lys | Ala | Leu | Ser | Thr | Leu | Gln | Arg | Ser | Ser | Leu | Val | Glu | Lys | Ser | Arg |

-continued

```
                405                 410                 415
Gln Lys Pro Glu Glu Arg Met Thr Val Leu Asn Asp Ala Leu Gln Arg
            420                 425                 430

Ser Asn Tyr Asp Ser Asp Pro Met Leu Arg Ala Cys Gly Val Ser Val
            435                 440                 445

Ala Pro Lys Phe Thr Gln Val Glu Gly Arg Ile Leu Gln Ala Pro Lys
450                 455                 460

Leu Lys Ala Gly Asn Gly Asp Asp Ile Phe Ser Arg Asn Gly Arg Trp
465                 470                 475                 480

Asn Phe Thr Asn Arg Lys Phe Tyr Glu Thr Cys Ser Val Asn Lys Trp
            485                 490                 495

Ala Val Val Asn Phe Ser Ala Arg Cys Asp Val Arg Asn Leu Ile Arg
            500                 505                 510

Asp Leu Met Arg Asn Ala Ser Ala Lys Gly Ile Gln Met Glu Glu Pro
            515                 520                 525

Phe Asp Val Phe Glu Glu Ser Pro Ser Met Arg Arg Ala Pro Val Ser
            530                 535                 540

Arg Arg Val Asp Asp Met Phe Gly Gln Ile Lys Ser Lys Leu Pro Gly
545                 550                 555                 560

Ala Pro Arg Phe Leu Leu Cys Leu Leu Pro Glu Arg Lys Asn Cys Glu
                565                 570                 575

Ile Tyr Gly Pro Trp Lys Arg Lys Cys Leu Ala Glu Phe Gly Ile Val
            580                 585                 590

Thr Gln Cys Leu Ala Pro Leu Arg Val Asn Asp Pro Tyr Leu Leu Asn
            595                 600                 605

Leu Leu Met Lys Ile Asn Ala Lys Leu Gly Gly Leu Asn Ser Leu Leu
            610                 615                 620

Gln Val Glu Ala Ser Ser Ser Ile Pro His Val Ser Gln Val Pro Thr
625                 630                 635                 640

Ile Ile Leu Gly Met Asp Val Ser His Gly His Pro Gly Gln Asp Arg
                645                 650                 655

Pro Ser Val Ala Ala Val Val Ser Ser Arg Gln Trp Pro Leu Ile Ser
                660                 665                 670

Arg Tyr Arg Ala Ser Val His Thr Gln Ser Ala Arg Leu Glu Met Met
            675                 680                 685

Ser Ser Leu Phe Lys Pro Arg Gly Thr Asp Asp Gly Leu Ile Arg
            690                 695                 700

Glu Ser Leu Ile Asp Phe Tyr Thr Ser Ser Gly Lys Arg Lys Pro Glu
705                 710                 715                 720

His Ile Ile Ile Phe Arg Asp Gly Val Ser Glu Ser Gln Phe Thr Gln
                725                 730                 735

Val Ile Asn Ile Glu Leu Asp Gln Ile Ile Glu Ala Cys Lys Phe Leu
            740                 745                 750

Asp Glu Lys Trp Ser Pro Lys Phe Thr Val Ile Val Ala Gln Lys Asn
            755                 760                 765

His His Thr Lys Phe Phe Gln Thr Ala Ser Pro Asp Asn Val Leu Pro
            770                 775                 780

Gly Thr Val Val Asp Ser Lys Val Cys His Pro Lys Asn Phe Asp Phe
785                 790                 795                 800

Tyr Met Cys Ala His Ala Gly Met Ile Gly Thr Thr Arg Pro Thr His
                805                 810                 815

Tyr His Val Leu His Asp Glu Ile Gly Phe Ser Ala Asp Glu Met Gln
            820                 825                 830
```

```
Glu Phe Val His Ser Leu Ser Tyr Val Tyr Gln Arg Ser Thr Thr Ala
        835                 840                 845

Ile Ser Val Ala Pro Val Cys Tyr Ala His Leu Ala Ala Ala Gln
    850                 855                 860

Val Ser Thr Phe Leu Arg Leu Glu Glu Met Ser Asp Ala Ser Ser
865                 870                 875                 880

Gln Gly Gly Gly His Thr Ser Ala Gly Ser Ala Pro Val Pro Glu Leu
                885                 890                 895

Pro Arg Leu His Asp Lys Val Arg Ser Ser Met Phe Phe Cys
                900                 905                 910

<210> SEQ ID NO 2
<211> LENGTH: 7896
<212> TYPE: DNA
<213> ORGANISM: Artificial Sequence
<220> FEATURE:
<223> OTHER INFORMATION: Description of Artificial Sequence: Synthetic
      genomic polynucleotide

<400> SEQUENCE: 2
taaacaagta acaacgact  atgtgtgcac  cagtgtctcc  tgtatcaacg  gggtggtccg     60
tctggaggag gtaccgaggt cccgccgttc gagagacgag ctacgcattt aagccgggga    120
ggtcggagca gtgagtggga gtagttcagg gactgggaga ggagaggaag caggacctgg    180
gagacctcgc ctcgtccgtc ctcctgccta cttccttgct tttggtaagt gaaagtgatt    240
gaagtggaga tgcctccaat ctgcagtgct gtttcacgcg taaaccctgg cccctcgcc     300 gctggaagcc cccattgttc ctctttcatt tcttaccgct gatgcagctt atggtttcct    360
agggttttcg agatatttgg tttcttgcat ccagaggacg aagagctttc atagggtttt    420
cgagacattg tcctcacaat cgcatccatt ttgcagtgct gtttcacgcg taaaccctag    480
cccctcgccg ctggaagcct ccattgttcc tctttcattt cttaccgctg atgcagctta    540
tggtttctta gggttttcga catttggc ttcttgcatc cagaggacga agagctttcc      600
tagggttttc gagacattgt cctcacattc gcagatttgg ttcgagacat tgttttttta    660
ggggttcaca tgtttctggg tgcttttgca gcgatgcgat tcatctcaca ggggatgggg    720
attcctacat taccgtgcct ttttttgggg aaaaatgccc actttttgtg taacaaaaac    780
ataaaaacga gccttgcagc tgcgatgtct gctgctcagg tggtttctca agaacaaatt    840 ttttaacaa aaaagccctt tcttttttct tactctcttg gaaagaaggt acatggagcc     900
aatccgttag gtcgctaact tcaccaaagg atttcatttt ccgtacctaa accttgtttc    960
aacaaaatgc tgccttggc cggggcatc tgattgtcat tttagtctgt tgattcttca     1020
agtcaatatt acgctcattt tattcaatgt ttcccgacag ccaactacac ttgtatttct    1080
ttgttagtaa cgtcccgcgc ttgagtcctt gtgatctgca cagtatgatg ctgccaccaa    1140
atgcatgcag ttagacaagc ttaatgttgc atctgataag actgtacaac agattcgtgt    1200
gccaaatgtg tccttgctac tcaaggaggt catatggaac aagtaaaacg aaatttctgc    1260
atcagcaatc aggcacaaga ctgaatgacg tggttagtgc caatgaggtg gggacttggg    1320
aatggaatta gagttatagc tattcctata attcatctca ctacagaggc tctccatcct    1380
actaggactg tacaacagat tcgtgtgcca atgtgtcct tgctactcaa ggaggtcata     1440
tggaacaagt aaaacaaaat ttctgcatca gcaatcaggc acaagactga atgacgtggt    1500
tagtgccaat gaggtgggaa cttgggaatg gaattagagt tatagctatt ctatagctat    1560
```

```
tcctataatt catctcacta cagaggctct ccatcctact agaatttaat ctgataaagt    1620
aggcagaaac atggaactta taatgtcgaa gattgcatgt atagaatcta agtaacggaa    1680
agattcaact ttgtgattat atgctgctgt tacatggtat tggtaaaaca ttctttcaag    1740
tgctcattgt cttcccttgc aaccaattca ttgttgtcct tgtttccttg caggtaggtg    1800
ctgcttgttt tatcttgaaa tgggctctca tgatggcgag gatgaagagt tgccaccccc    1860
ccctccggtg ccaccagatg tgattcccat taaagctgaa gatgctgtgg gtgaatcacc    1920
agcaaaccat atattaaagc caaagagatt actgatggac aggcctggta taggaagaaa    1980
agggcagccg acccagctct attcaaatca ctttaaagtc gctgtgaaga gtacagaaga    2040
cgtcttcttt cactactatg tatgtctgct gactgagttc atgatccttt gttcaaaata    2100
tgtcattgtc tgtcccttgt ttataactaa tctttggctg atgtgatatt gttattttat    2160
ttgactaggt aaacctgaag tatgaggatg atcgacccgt tgatggtaaa gggatcggca    2220
gaaaggtgat tgataaactg cagcagacat atcgtgcaga gctttctaac aaggactttg    2280
catatgatgg agaaaagagc ctgtttacag ttggtggtct tccacaaaaa aagaatgagt    2340
tcaccgttgt cttggaggac gtatctactg gaaagttagt tttagtcttt gatctgcttt    2400
cttgttgttt atgcttaccc agaatcagta attgccatgt tttttgtttg tggttgtagg    2460
actgctgcca atgggagccc tggaggtaat gacagtcctg gaggtggtga taggaagaga    2520
gtgaggaggc ataccagac gaaaactttc aaagtggaga taaattttgc agcagaggtt    2580
cctatgagtg ctattggtca agtcattaga ggcgaagaat ctgagaactc cctggaggcg    2640
cttcgtgttc ttgatatcat actgaggcag cattccgcag aacagtatgt agctatgcat    2700
cttgatggat gattataggt agatttgagg atcttctgca gttacgacat gacaatttt    2760
ctcaatactt gcagaggctg ccttttggtt aagcaatcat ttttctacaa caacccttca    2820
tgctttgttg acttgggtgg tggtgtgatg ggttgtcgtg gatttcattc aagcttccgt    2880
ggcacacaga gtggactttc cctcaatgtt ggtgcgtgtt cgtcctgtat ggctgtattg    2940
gtgccatgta actgcattgt ctattctata atcttacatc tttcatgatc atgatagcct    3000
ttttttttga aatccacaga tgtctcaaca acaatgatcg tgaaacctgg ccctgttatt    3060
gattttcttc tttctaacca gaatgttaat gatcctagca gaattgattg gcaaaaggta    3120
aatgccatct ttggatgaaa cttctcgaat aaccatgcta gtgcattgaa atatctatt    3180
tgatagaatg ataacacaat tttggggtgt gcatattcaa tacaggccaa gcgtgctctc    3240
aagggcttga ggattagaac cactcctgca aattcagaat tcaagatttt tggtctcagc    3300
gagaggatct gcaaagaaca aacgtgtgga catgttttct taccgctctg tttattgtca    3360
tgcaagcttt actttacatt tttaaaaaat tgtaccctag tgtgttaagc ttgtttcaga    3420
agaattttat ttaacaaata ttgcctttat tgattttgtt ctgattccaa tgccaagctt    3480
gcttgatggt gatatctgtg tgcttaattg cttctcatt gacatatgca attaggtttc    3540
cgctgaggca gagaaatggt agcaacggag attgtgatac cattgaaata actgtctatg    3600
actactatgc aaagaaagga atcgatctaa agtattctgg tgatttcccc tgtataaata    3660
cagggaaggc aaagcgccca acatatttc caatcgaggt ttgtttcagt tttgttagtt    3720
acatcctgtc aaatctctgt ttattaaata tatcttgcat ctcatattcg atgggcaggc    3780
ttggtggggc tgtctcactg agtcactagg tcgtgggttc aaagcagcct ctccacattt    3840
gtggggggg gaaggcttgc ttcggtttat cccttcctta gacccctaggt ctgcccctt    3900
ttttgcatct cattttttg tattgtgttt ctagctatgc tcgcttgttc cgcttcaaag    3960
```

```
atacaccaaa gctttgtcta cgctacaaag gtcatccctt gtggagaagt ctagacagaa    4020
gcctgaagaa aggatgaccg ttctaaatga tgtgagctgt taccttgatt ttagcatgct    4080
gcgaccattc ataactgcat gggatttatt tctacgactg aattaatcaa cagcttatga    4140
ttaccctaaa tgctaggcac tgcaacgcag taactacgat tctgacccca tgttgagggc    4200
atgtggtgtt tcagttgctc caaaatttac ccaagttgaa ggaaggatcc ttcaagcccc    4260
aaaggttggt gacacttctc taagctttac gacaagtttg catggaaatc taaaatttgg    4320
atcatggata aaaataatct ctggtgttta ttggattctg tgcttgttag agaatcctag    4380
ggtgtttgga tggaattcta ggatttaaag attttttttcc tatcctgatt gttaatatct    4440
ctatggatcc aaacgctccc ttagttgttt tctctctaaa tgttgtacca agtcattatc    4500
tcagtaaaat gcatctgact aaatctaata tcttgtagct gaaagccggc aatggtgatg    4560 atatctttc acgaaatgga cggtggaatt tcactaatag ggtcagcagc tcaacatgtt    4620 tctttttaa ccttctttag ttctttatta ggaaggattt ttctgatgtt tatttgccaa    4680
tactttgccc ctttcagaag ttttatgaaa cctgctctgt gaataagtgg gcggtcgtta    4740
atttctctgc acgttgtgat gttcggaatc ttatccgtga cctgatgagg aatgcatctg    4800
caaagggaat tgtatggttt agcttttcac atatcttcta ttgtagcagt tttctgctgc    4860
tgacgttttt cttctggcag caaatggagg aaccttttga tgtgtttgaa gagagtccct    4920
ctatgaggcg tgcacctgtg tcaagaaggg tggatgatat gtttgggcag ataaaatcaa    4980
aacttcctgg agctcctagg ttcctcttgt gccttctccc tgagaggaaa aattgtgaaa    5040
tctatggttg gtttatttt tgttaccact ccacataaat atctcacatc ttgcaataat    5100 tataccttt tggtttcaac caggtccttg gaagagaaag tgcctggccg agtttggtat    5160
tgtcacacag tgtctagctc cattaagagt caatgatccg tacctgctta atttgctgat    5220
gaagatcaat gcaaaggttt gggacatgat tttgtctttc ttttgcactg tattgttccc    5280
tggttcatga ttatattatc ctcttcctc tgttttaaac tagcttggtg gtctgaactc    5340
gttgctgcaa gttgaagcat cttcgtcaat accacatgtg tcgcaagtac ccaccatcat    5400
cttaggtatg gatgtttcac atggtcatcc aggacaagat agaccttcgg ttgcagcggt    5460
aagatgggtg taccttttact tgtacaattc ttctgcccac atggaatctg agtggttttg    5520
taaaatatgt gaaatggatg tctgttaatc tgatgtaaac cataccttc ttctttgttt    5580 aggtggttag ttctcgtcaa tggcctctta tctctagata tagagcatca gtgcacaccc    5640
aatctgccag actagaaatg atgtcctcgt tgtttaagcc gcggggtact gatgatgatg    5700
gcctcatccg gtaagagata tcttcttagt atgttgatgt atggtaagcg tgatgacttt    5760
tggatgctaa gtttatcttc gtatttggga cttccaggga atcactgatc gacttctaca    5820
ctagctctgg aaagcgaaaa ccagaacaca taattatttt caggtctgaa gctttgggt    5880 tattgttagc ttgtatcact aaatctttt gtagaaacaa attctttttt ttgttttgt    5940 tttgagaagt atgtatggta cattctttgc tgggatggat tattgatact ttcttagccg    6000
ccgtggcgta aatgtaacca tttgctgggt tttagggatg gagtcagtga aagtcagttt    6060
acccaggtca tcaacattga gctggatcag atcatcgagg taatacattt gtttgattcg    6120
tcctttgcac atttgcttgc ttagttcagg aacgaattgc aaggtaacac atccttgtaa    6180
ttaatgcagg catgtaagtt tctggatgag aagtggtcac ccaagttcac tgtgattgtt    6240
gctcaaaaga accaccacac caagttcttt cagacggcat caccagacaa tgttcttcct    6300
```

-continued

```
ggtaatatgt ttattttgt catactaaag ggagtgtggt gagatgcggt gacaataata      6360
aatgtgtttg tttgttacgc aggaactgtg gtggatagta aagtttgcca tcctaagaac      6420
ttcgacttct acatgtgtgc acatgctggg atgattgtga gttgatctca gaattgagca      6480
aaaagatgct gctgtcttgt tcttgtctct gaatcctaga tggttcttcg tctcagggaa      6540
caacaaggcc gacccactat catgttctgc acgacgagat aggtttcagt gccgacgaga      6600
tgcaggagtt tgttcattcg ctctcttacg tgtaagtagt agtagtaaaa tgctgttttg      6660
gctgtgtgtg tgtgtgtgtg ttttgtgctt acgctgcgtg tcctgctgtg caggtaccag      6720
aggagcacga cagccatctc agtgggtagg ccgcttgaat ctaaagccat cttgtgcagc      6780
acagggacag caggttgatt ttttctagt gtctgttttt gtgtttgcag ttgctccagt       6840
gtgctacgcc cacctcgctg cagcccaggt gagcacgttc ctgagattgg aggagatgtc      6900
agacgcgtcc tccagccagg gaggagggca tacctcggct ggcagtgctc ctgtgccgga      6960
gctgcctcgc ctgcatgaca aagtcaggag ctccatgttc ttctgctagc tgatgtgcgt      7020
gcgcatcagg atcgagctcc atgttttgtg ttagtaaggc ctagttagta aggctgtaga      7080
aagaatgttt aatgtttgca tgctaaagtc caaacaatca aaccactac tatatctacc       7140 agagcactga tcgatcaaac aacaagagtc agcatcaatc aatcaaaacc accactattc      7200
tatctaccga tcaatctact ctatacctga agcactcact cgctcgcaaa caaccaaggg      7260
atcatggatc cttgagtagc tccattgtcc agtccctgac cttgacgaag catttcatgg      7320
acagcctctc gtacgccatc tcgtacatcc ggaggttcat gtaggcgaag ctcaagtagg      7380
tggcgatgca ctcttggtgc ctgtggtaca gcgccgggat ggtcagagcg gccaccacac      7440
ttgcgtagca ggcggtcggg aaatctgtaa cgctgccgac gatggacacg ctccacaggc      7500
agaggaaggc tctgtagaag agcagcgagt ccctgcccag agcgatgtcc cggaaagcgt      7560
ccgaggcggc gtccagagca gagcgcagca gcgccgccgc ctcgtccacg gcctgctgcg      7620
gaacgcgcag ctccgggacg ggaggctgcg gcctgttcag gaggcgcgcc gctttggccc      7680
acaggaagag cacggtgagg agcaggagca gcacgttgga ggcgagggac accaaggtgt      7740
agccgccgta caagagcagc caggaggaga cggtgcccgc cagcaggcag gcgctcacgt      7800
cggcgcggcc ccggcgccac agcagcacgt cccagactgc tgcagcaatc cgatccgatt      7860
ccgatccaga tatattagtt agtagatcca atctcg                               7896
```

<210> SEQ ID NO 3
<211> LENGTH: 3015
<212> TYPE: DNA
<213> ORGANISM: Artificial Sequence
<220> FEATURE:
<223> OTHER INFORMATION: Description of Artificial Sequence: Synthetic
      transcript polynucleotide

<400> SEQUENCE: 3

```
ggagaggaag caggacctgg gagacctcgc ctcgtccgtc ctcctgccta cttccttgct       60
tttggtaggt gctgcttgtt ttatcttgaa atgggctctc atgatggcga ggatgaagag      120
ttgccacccc ccctccggt gccaccagat gtgattccca ttaaagctga agatgctgtg      180
ggtgaatcac cagcaaacca tatattaaag ccaaagagat tactgatgga caggcctggt      240
ataggaagaa aagggcagcc gacccagctc tattcaaatc actttaaagt cgctgtgaaa      300
gtacagaaga cgtcttcttt cactactatg taaacctgaa gtatgaggat gatcgacccg      360
ttgatggtaa agggatcggc agaaaggtga ttgataaact gcagcagaca tatcgtgcag      420
```

-continued

```
agctttctaa caaggacttt gcatatgatg gagaaaagag cctgtttaca gttggtggtc      480
ttccacaaaa aaagaatgag ttcaccgttg tcttggagga cgtatctact ggaaagactg      540
ctgccaatgg gagccctgga ggtaatgaca gtcctggagg tggtgatagg aagagagtga      600
ggaggccata ccagacgaaa actttcaaag tggagataaa ttttgcagca gaggttccta      660
tgagtgctat tggtcaagtc attagaggcg aagaatctga gaactccctg gaggcgcttc      720
gtgttcttga tatcatactg aggcagcatt ccgcagaaca aggctgcctt ttggttaagc      780
aatcattttt ctacaacaac ccttcatgct ttgttgactt gggtggtggt gtgatgggtt      840
gtcgtggatt tcattcaagc ttccgtggca cacagagtgg actttccctc aatgttgatg      900
tctcaacaac aatgatcgtg aaacctggcc ctgttattga ttttcttctt tctaaccaga      960
atgttaatga tcctagcaga attgattggc aaaaggccaa gcgtgctctc aagggcttga     1020
ggattagaac cactcctgca aattcagaat tcaagatttt tggtctcagc gagaggatct     1080
gcaaagaaca aacgtttccg ctgaggcaga gaaatggtag caacggagat tgtgatacca     1140
ttgaaataac tgtctatgac tactatgcaa agaaaggaat cgatctaaag tattctggtg     1200 atttccctg tataaataca gggaaggcaa agcgcccaac atattttcca atcgagctat     1260
gctcgcttgt tccgcttcaa agatacacca aagctttgtc tacgctacaa aggtcatccc     1320
ttgtggagaa gtctagacag aagcctgaag aaaggatgac cgttctaaat gatgcactgc     1380
aacgcagtaa ctacgattct gacccccatgt tgagggcatg tggtgtttca gttgctccaa     1440
aatttaccca agttgaagga aggatccttc aagccccaaa gctgaaagcc ggcaatggga     1500
tgatatcttt tcacgaaatg gacggtggaa tttcactaat aggaagtttt atgaaacctg     1560
ctctgtgaat aagtgggcgg tcgttaattt ctctgcacgt tgtgatgttc ggaatcttat     1620
ccgtgacctg atgaggaatg catctgcaaa gggaattcaa atggaggaac cttttgatgt     1680
gtttgaagag agtccctcta tgaggcgtgc acctgtgtca agaagggtgg atgatatgtt     1740
tgggcagata aaatcaaaac ttcctggagc tcctaggttc ctcttgtgcc ttctccctga     1800
gaggaaaaat tgtgaaatct atggtccttg gaagagaaag tgcctggccg agtttggtat     1860
tgtcacacag tgtctagctc cattaagagt caatgatccg tacctgctta atttgctgat     1920
gaagatcaat gcaaagcttg gtggtctgaa ctcgttgctg caagttgaag catcttcgtc     1980
aataccacat gtgtcgcaag tacccaccat catcttaggt atggatgttt cacatggtca     2040
tccaggacaa gatagacctt cggttgcagc ggtggttagt tctcgtcaat ggcctcttat     2100
ctctagatat agagcatcag tgcacaccca atctgccaga ctagaaatga tgtcctcgtt     2160
gtttaagccg cggggtactg atgatgatgg cctcatccgg gaatcactga tcgacttcta     2220
cactagctct ggaaagcgaa aaccagaaca cataattatt ttcagggatg gagtcagtga     2280
aagtcagttt acccaggtca tcaacattga gctggatcag atcatcgagg catgtaagtt     2340
tctggatgag aagtggtcac ccaagttcac tgtgattgtt gctcaaaaga accaccacac     2400
caagttcttt cagacggcat caccagacaa tgttcttcct ggaactgtgg tggatagtaa     2460 agttttgccat cctaagaact tcgacttcta catgtgtgca catgctggga tgattggaac     2520
aacaaggccg accccactatc atgttctgca cgacgagata ggtttcagtg ccgacgagat     2580
gcaggagttt gttcattcgc tctcttacgt gtaccagagg agcacgacag ccatctcagt     2640
ggttgctcca gtgtgctacg cccacctcgc tgcagcccag gtgagcacgt tcctgagatt     2700
ggaggagatg tcagacgcgt cctccagcca gggaggaggg catacctcgg ctggcagtgc     2760
tcctgtgccg gagctgcctc gcctgcatga caaagtcagg agctccatgt tcttctgcta     2820
```

```
gctgatgtgc gtgcgcatca ggatcgagct ccatgttttg tgttagtaag gcctagttag    2880
taaggctgta gaaagaatgt ttaatgtttg catgctaaag tccaaacaat caaaaccact    2940
actatatcta ccagagcact gatcgatcaa acaacaagag tcagcatcaa tcaatcaaaa    3000
ccaccactat tctat                                                     3015

<210> SEQ ID NO 4
<211> LENGTH: 2733
<212> TYPE: DNA
<213> ORGANISM: Artificial Sequnce
<220> FEATURE:
<223> OTHER INFORMATION: Description of Artificial Sequence: Synthetic
      Orf polynucleotide

<400> SEQUENCE: 4
atgggctctc atgatggcga ggatgaagag ttgccacccc ccctccggt gccaccagat       60 gtgattccca ttaaagctga agatgctgtg ggtgaatcac cagcaaacca tatattaaag     120
ccaaagagat tactgatgga caggcctggt ataggaagaa aagggcagcc gacccagctc     180
tattcaaatc actttaaagt cgctgtgaag agtacagaag acgtcttctt tcactactat     240
gtaaacctga gtatgagga tgatcgaccc gttgatggta aagggatcgg cagaaaggtg      300
attgataaac tgcagcagac atatcgtgca gagctttcta caaggacttt gcatatgat     360 ggagaaaaga gcctgtttac agttggtggt cttccacaaa aaagaatga gttcaccgtt     420 gtcttggagg acgtatctac tggaaagact gctgccaatg ggagccctgg aggtaatgac    480
agtcctggag gtggtgatag gaagagagtg aggaggccat accagacgaa aactttcaaa    540
gtggagataa attttgcagc agaggttcct atgagtgcta ttggtcaagt cattagaggc    600
gaagaatctg agaactccct ggaggcgctt cgtgttcttg atatcatact gaggcagcat    660
tccgcagaac aaggctgcct tttggttaag caatcatttt tctacaacaa cccttcatgc    720
tttgttgact gggtggtgg tgtgatgggt tgtcgtggat tcattcaag cttccgtggc     780 acacagagtg gactttccct caatgttgat gtctcaacaa caatgatcgt gaaacctggc    840
cctgttattg attttcttct ttctaaccag aatgttaatg atcctagcag aattgattgg    900
caaaaggcca gcgtgctct caagggcttg aggattgaa ccactcctgc aaattcagaa     960
ttcaagattt ttggtctcag cgagaggatc tgcaaagaac aaacgtttcc gctgaggcag   1020
agaaatggta gcaacggaga ttgtgatacc attgaaataa ctgtctatga ctactatgca   1080
aagaaaggaa tcgatctaaa gtattctggt gatttccct gtataaatac agggaaggca    1140
aagcgcccaa catattttcc aatcgagcta tgctcgcttg ttccgcttca agatacacc    1200 aaagctttgt ctacgctaca aaggtcatcc cttgtggaga agtctagaca gaagcctgaa   1260
gaaaggatga ccgttctaaa tgatgcactg caacgcagta actacgattc tgaccccatg   1320
ttgagggcat gtggtgtttc agttgctcca aaatttaccc aagttgaagg aaggatcctt   1380
caagccccaa agctgaaagc cggcaatggt gatgatatct tttcacgaaa tggacggtgg   1440
aatttcacta ataggaagtt ttatgaaacc tgctctgtga ataagtgggc ggtcgttaat   1500
ttctctgcac gttgtgatgt tcggaatctt atccgtgacc tgatgaggaa tgcatctgca   1560
aagggaattc aaatggagga accttttgat gtgtttgaag agagtccctc tatgaggcgt   1620
gcacctgtgt caagagggt ggatgatatg tttgggcaga taaaatcaaa acttcctgga   1680
gctcctaggt tcctcttgtg ccttctccct gagaggaaaa attgtgaaat ctatggtcct   1740
tggaagagaa agtgcctggc cgagtttggt attgtcacac agtgtctagc tccattaaga   1800
```

```
gtcaatgatc cgtacctgct taatttgctg atgaagatca atgcaaagct tggtggtctg    1860
aactcgttgc tgcaagttga agcatcttcg tcaataccac atgtgtcgca agtacccacc    1920
atcatcttag gtatggatgt ttcacatggt catccaggac aagatagacc ttcggttgca    1980
gcggtggtta gttctcgtca atggcctctt atctctagat atagagcatc agtgcacacc    2040
caatctgcca gactagaaat gatgtcctcg ttgtttaagc cgcggggtac tgatgatgat    2100
ggcctcatcc gggaatcact gatcgacttc tacactagct ctggaaagcg aaaaccagaa    2160
cacataatta ttttcaggga tggagtcagt gaaagtcagt ttacccaggt catcaacatt    2220
gagctggatc agatcatcga ggcatgtaag tttctggatg agaagtggtc acccaagttc    2280
actgtgattg ttgctcaaaa gaaccaccac accaagttct ttcagacggc atcaccagac    2340
aatgttcttc ctggaactgt ggtggatagt aaagtttgcc atcctaagaa cttcgacttc    2400
tacatgtgtg cacatgctgg gatgattgga acaacaaggc cgacccacta tcatgttctg    2460
cacgacgaga taggtttcag tgccgacgag atgcaggagt tgttcattc gctctcttac    2520 gtgtaccaga ggagcacgac agccatctca gtggttgctc agtgtgcta cgcccacctc    2580 gctgcagccc aggtgagcac gttcctgaga ttggaggaga tgtcagacgc gtcctccagc    2640
cagggaggag ggcatacctc ggctggcagt gctcctgtgc cggagctgcc tcgcctgcat    2700
gacaaagtca ggagctccat gttcttctgc tag                                 2733
```

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      anticorps peptide

<400> SEQUENCE: 5

Ser Glu Arg Ile Cys Lys Glu Gln Thr Phe Pro Leu Arg Gln Arg
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      anticorps peptide

<400> SEQUENCE: 6

Val Ser Thr Phe Leu Arg Leu Glu Glu Met Ser Asp Ala
1               5                   10

<210> SEQ ID NO 7
<211> LENGTH: 11129
<212> TYPE: DNA
<213> ORGANISM: Artificial sequence
<220> FEATURE:
<223> OTHER INFORMATION: Description of Artificial Sequence: Synthetic
      mutant polynucleotide
<220> FEATURE:
<221> NAME/KEY: modified_base
<222> LOCATION: (3102)..(3111)
<223> OTHER INFORMATION: a, c, t or g
<220> FEATURE:
<221> NAME/KEY: modified_base
<222> LOCATION: (6223)..(6232)
<223> OTHER INFORMATION: a, c, t or g
<220> FEATURE:
<221> NAME/KEY: modified_base
<222> LOCATION: (6310)..(6319)
<223> OTHER INFORMATION: a, c, t or g
<220> FEATURE:
<221> NAME/KEY: modified_base
<222> LOCATION: (6325)..(6326)
<223> OTHER INFORMATION: a, c, t or g

<400> SEQUENCE: 7

```
tacacaagag gagcgaagca agtttcatcc aacaggcttc atcacggtga aacgggtata      60
caacgtggct tcggtataac tcaaaggaag tataacgaag cacacttcat caagcaggct     120
tcgtcataac gaaacaatga gatgcaagga gaaggtgtta ctcaagttat taaatacaac     180
tgacgacatt gcccttatga catattgtaa actctgtatg taattattga gggtataaat     240
gtaatagcgt acgaacccttt gcgattgtct ataaatagat gaacattacc ccgtactatt     300
cacgttggat tgtaatcgct ctcgcgtcaa caccttcaaa caagccgaag atatcactgc     360
aatataaatt ttgataatgt ttatatattt atcatggaat aaatatatga ctggatatca     420
cactcatgta tttaaatcct tattgatata aatgatgagg atgtgttatt cacgaccttt     480
gtctgaagat tattatatcc gaaaggagat attttttcga aggacgaatg ttcttaacat     540
ttaataactg tgttaccttg ttcttgaaca tgtgacaaac attaggtttt gagtatttca     600
attaatagtg aaattaaatt aaattttagt tgtccaaaat gacagacttc gatatttgtt     660
ataattgttg agttaaattt taacagcatc cataaacaag taaacaacga ctatgtgtgc     720
accagtgtct cctgtatcaa cggggtggtc cgagataagt gctattatgg acgaagaggg     780
aaggggattc gacgaaatgg aggcgttggc gttggcttct gtgttttgga gacgcacgcg     840
acagccaaac tccaaaacgg atacgagaca gctcttgggg ctgcgtaaac aggtattagt     900
tttctgtccc cgtttaccgt tcccgtgcgc agacgccgtc acgcgtactc ttcttgtctc     960
cgtcgccgcg ctctacggcg gtgctggcgt ccgtgctgta ctccgcgccg gcagaggccg    1020
cgcgcgcgtc gcccgcggac ggcgccacgc cgctccacct cgccgcggcc gtgcacatcc    1080
tcctcgccgc gggcgcgtcc gtggacgcgc gcgccttctc gggcctccgc gccggggacc    1140
tcctcctccc gcgcgccaac gaggccgccg ccgccgcaga ccgggcgctc cgcgtgctcc    1200
tgaagttccc cgcggcgtca ctgtcgtcct cgcccaagaa gtccgcctcg ccgccgccgg    1260
ccccggaggc gaggaaggag tacccgcccg acctgacgct gccggacctc aagagcgggc    1320
tgttcagcac cgacgagcaa cggacgcacc ttacagctgt cctagcacta attactccta    1380
aattcatcat acaccaaagt ttcaattagt aaaaggtttt ggtattattt tctttacaag    1440
actaaaagca tccactcgta tttgccatgg aaatattgcc aaaatggtta ccgaagaacc    1500
aatgaaaaat ggcggtatcc gtccacctgt aacttgtcca aggctcttcc agcagagtag    1560
tgccgccatg acgattgaca gagacacgag acgaaacaag cagaaggtcc ccgcggcgtc    1620
actgtcgtcc tcgcccaaga agtccgcctc gccgccgccg gccccggagg cgaggaagga    1680
gtacccgccc gacctgacgc tgccggacct caagagcggg ctgttcagca ccgacgagtt    1740
ccgcatgtac agcttcaagg tgaagccctg ctcccgcacc tactcgcaca actggaccga    1800
gtgcccttcg tgcaccccggg cgagaacgcg cggcgccgtg accgcgcgt actcctacag    1860
ctgcgtgccc tgcccgagt tccgcaaggg ccggcgctgc cgcaagggcg acggctgcga    1920
gtacgcgcac gacgtcttcg agtgctggct ccaccccggc gcagtaccgg acgcgcctct    1980
gcaaggacga ggtgggctgc gcgcgccgca tctgcttctt cgcgcacaag cgcgaggagc    2040
tccgcgccgt caacccctcc gcggtgttcg tcggcatgca gatgcagccc accgtgtcgc    2100
```

```
cgccgccgcc caacggcctc ggcgacatgc tcagcccggc ggcctggccc tcctcccccg    2160
cgagcaggct caataaggcc gcgctcggcg gccgggacct ggaccagtac cagcacatgt    2220
tgttcgacaa ggtgtcgtcg ccgagggcca gttggagaca agaagagtac gcgtgacgga    2280
gatgcgacgg agaaaaaggg tacgcgtgac ggcgtctgca cacgggaacg gtaaacgggg    2340
acaagaaact aatacctgtt tacgcagccc caagtgctgt ctcgtatccg tttggagtt     2400
tggctgtcgc gtgcgtctcc aaaacagaga agccaacgcc aacgcctcca tttcgtcgaa    2460
tccccttccc tcttcgtcca taatggcaat tatctcctcg tgttcgtctg gaggaggtac    2520
cgaggtcccg ccgttcgaga gacgagctac gcatttaagc cggggaggtc ggagcagtga    2580
gtgggagtag ttcagggact gggagaggag aggaagcagg acctgggaga cctcgcctcg    2640
tccgtcctcc tgcctacttc cttgcttttg gtaagtgaaa gtgattgaag tggagatgcc    2700
tccaatctgc agtgctgttt cacgcgtaaa ccctggcccc ctcgccgctg gaagccccat    2760
tgttcctctt tcatttctta ccgctgatgc agcttatggt ttcctagggt tttcgagata    2820
tttggtttct tgcatccaga ggacgaagag ctttcatagg gttttcgaga cattgtcctc    2880
acaatcgcat ccattctgca gtgctgtttc acgcgtaaac cctagcccct cgtcgctgga    2940
agcccacatg gttcctcttt catttcttac cgctgatgca gcttatgggt cctagggtt    3000
ttcgagacat ttggcttctt gcatccagag gacgaagagc tttcctaggg ttttcgagac    3060
attgtcctca caatcgcaga tttggttcga gacatttgtt tnnnnnnnnn ncgtcccgcg    3120
cttgagtcct tgtgatctgc acagcatgat gctgccacca aatgcatgca gttagacaag    3180
cttaatgttg catctgataa gactgtacaa cagattcgtg tgccaaatgt gtccttgcta    3240
ctcaaggagg tcatatggaa caagtaaaac gaaatttctg catcagcaat caggcacaag    3300
actgaatgac gtggttagtg ccaatgaggt ggggacttgg gaatgaatt agagttatag     3360
ctattcctat aattcatctc actacagagg ctctccatcc tactaggact gtacaacaga    3420
ttcgtgtgcc aaatgtgtcc ttgctactca aggaggtcat atggaacaag taaaacaaaa    3480
tttctgcatc agcaatcagg cacaagactg aatgacgtgg ttagtgccaa tgaggtggga    3540
acttgggaat ggaattagag ttatagctat tcctataat tcctataat tcatctcact     3600
acagaggctc tccatcctac tagaatttaa tctgataaag taggcagaaa catggaactt    3660
ataatgtcga agattgcatg tatagaatct aagtaacgga aagattcaac tttgtgatta    3720
tatgctgctg ttacatggta ttggtaaaac attctttcaa gtgctcattg tcttcccttg    3780
caaccaattc attgttgtcc ttgtttcctt gcaggtaggg gctgcttgtt ttatcttgaa    3840
atgggctctc atgatggcga ggatgaagag ttgccacccc cccctccggt gccaccagat    3900
gtgattccca ttaaagctga agatgctgtg ggtgaatcac cagcaaacca tatattaaag    3960
ccaaagagat tactgatgga caggcctggt ataggaagaa aagggcagcc gacccagctc    4020
tattcaaatc acttaaagt cgctgtgaag agtacagaag acgtcttctt tcactactat     4080
gtatgtctgc tgactgagtt catgatcctt tgttcaaaat atgtcattgt ctgtcccttg    4140
tttataacta atctttggct gatgtgatat tgttatttta tttgactagg taaacctgaa    4200
gtatgaggat gatcgacccg ttgatggtaa agggatcggc agaaaggtga ttgataaact    4260
gcagcagaca tatcgtgcag agctttctaa caaggacttt gtatatgatg gagaaaagag    4320
cctgttttaca gttggtggtc ttccacaaaa aaagaatgag ttcaccgttg tcttggagga    4380
cgtatctact ggaaagttag ttttagtctt tgatctgctt tcttgttgtt tatgcttacc    4440
cagaatcagt aattgccatg tttttttgttt gtggttgtag gactgctgcc aatgggagcc    4500
```

```
ctggaggtaa tgacagtcct ggaggtggtg ataggaagag agtgaggagg ccataccaga    4560
cgaaaacttt caaagtggag ataaattttg cagcagaggt tcctatgagt gctattggtc    4620
aagtcattag aggcgaagaa tctgagaact ccctggaggc gcttcgtgtt cttgatatca    4680
tactgaggca gcattccgca gaacagtatg tagctatgca tcttgatgga tgattatagg    4740
tagatttgag gatcttctgc agttacgaca tgacaatttt tctcaatact gcagaggct    4800 gccttttggt taagcaatca ttttttctaca acaacccttc atgctttgtt gacttgggtg    4860
gtggtgtgat gggttgtcgt ggatttcatt caagcttccg tggcacacag agtggacttt    4920
ccctcaatgt tggtgcgtgt tcgtcctgta tggctgtatt ggtgccatgt aactgcattg    4980
tctattctat aatcttacat cttctcatgat catgatagcc ttttttttg aaatccacag    5040 atgtctcaac aacaatgatc gtgaaacctg gccctgttat tgattttctt ctttctaacc    5100
agaatgttaa tgatcctagc agaattgatt ggcaaaaggt aaatgccatc tttggatgaa    5160
acttctcgaa taaccatgct agtgcattga aatatctatt ttgatagaat gataacacaa    5220
ttttggggtg tgcatattca atacaggcca agcgtgctct caagggcttg aggattagaa    5280
ccactcctgc aaattcagaa ttcaagattt ttggtctcag cgagaggatc tgcaaagaac    5340
aaacgtgtgg acatgttttc ttaccgctct gtttattgtc atgcaagctt tactttacat    5400
ttttaaaaaa ttgtacccta gtgtgttaag cttgtttcag aagaatttta tttaacaaat    5460
attgccttta ttgattttgt tctgattcca atgccaagct tgcttgatgg tgatatctgt    5520
gtgcttaatt gcttttctcat tgacatatgc aattaggttt ccgctgaggc agagaaatgg    5580
tagcaacgga gattgtgata ccattgaaat aactgtctat gactactatg caaagaaagg    5640
aatcgatcta aagtattctg gtgatttccc ctgtataaat acaggggaagg caaagcgccc    5700 aacatatttt ccaatcgagg tttgtttcag ttttgttagt tacatcctgt caaatctctg    5760
tttattaaat atatcttgca tctcatattc gatgggcagg cttggtgggg ctgtctcact    5820
gagtcactag gtcgtgggtt caaagcagcc tctccacatt tgtgggggggg ggaaggcttg    5880 cttcggttta tccctttcctt agaccctagg tctgccccctt tttttgcatc tcattttttt    5940
gtattgtgtt tctagctatg ctcgcttgtt ccgcttcaaa gatacaccaa agctttgtct    6000
acgctacaaa ggtcatccct tgtggagaag tctagacaga agcctgaaga aaggatgacc    6060
gttctaaatg atgtgagctg ttaccttgat tttagcatgc tgcgaccatt cataactgca    6120
tgggatttat ttctacgact gaattaatca acagcttatg attaccctaa atgctaggca    6180
ctgcaacgca gtaactacga ttctgacccc atgttgatgt gcnnnnnnnn nnaggttgag    6240
ggcatgtggt gtttcagttg ctccaaaatt tacccaagtt gaaggaagga tccttcaagc    6300
cccaaaggtn nnnnnnnnng cttgnnagag aatcctaggg tgtttggatg gaattctagg    6360
atttaaagat tttttttccta tcctgattgt taatatctct atggatccaa acgctccctt    6420
agttgttttc tctctaaatg ttgtaccaag tcattatctc agtaaaatgc atctgactaa    6480
atctaatatc ttgtagctga aagccggcaa tggtgatgat atcttttcac gaaatggacg    6540
gtggaatttc actaataggg tcagcagctc aacatgtttc tttttttaacc ttctttttt    6600 ctttattagg aaggattttt ctgatgttta tttgccaata ctttgcccct tcagaagtt    6660 ttatgaaacc tgctctgtga ataagtgggc ggtcgttaat ttctctgcac gttgtgatgt    6720
tcggaatctt atccgtgacc tgatgaggaa tgcatctgca aagggaattg tatggtttag    6780
cttttcacat atcttctatt gtagcagttt tctgctgctg acgttttctt ctggcagcaa    6840
```

```
atggaggaac cttttgatgt gtttgaagag agtccctcta tgaggcgtgc acctgtgtca    6900
agaagggtgg atgatatgtt tgggcagata aaatcaaaac ttcctggagc tcctaggttc    6960
ctcttgtgcc ttctccctga gaggaaaaat tgtgaaatct atggttggtt tattttttgt    7020
taccactcca cataaatatc tcacatcttg caataattat accttttttgg tttcaaccag    7080 gtccttggaa gagaaagtgc ctggccgagt ttggtattgt cacacagtgt ctagctccat    7140
taagagtcaa tgatccgtac ctgcttaatt tgctgatgaa gatcaatgca aaggtttggg    7200
acatgatttt atctttcttt tgcactgtat tgttccctgg ttcatgatta tattatcctc    7260
tttcctctgt ttttaactag cttggtggtc tgaactcgtt gctgcaagtt gaagcatctt    7320
cgtcaatacc acatgtgtcg caagtaccca ccatcatctt aggtatggat gtttcacatg    7380
gtcatccagg acaagataga ccttcggttg cagcggtaag atgggtgtac ctttacttgt    7440
acaattcttc tgcccacatg aatctgagt ggttttgtaa aatatgtgaa atggatgtct    7500
gttaatctga tgtaaaccat accttttcttc tttgttttagg tggttagttc tcgtcaatgg    7560
cctcttatct ctagatatag agcatcagtg cacacccaat ctgccagact agaaatgatg    7620
tcctcgttgt ttaagccgcg gggtactgat gatgatggcc tcatccggta agagatatct    7680
tcttagtatg ttgatgtatg gtaagcgtga tgacttttgg atgctaagtt tatcttcgta    7740
tttgggactt ccagggaatc actgatcgac ttctacacta gctctggaaa gcgaaaacca    7800
gaacacataa ttatttttcag gtctgaagct ttggggttat tgttagcttg tatcactaaa    7860 tcttttttgta gaaacaaatt cttttttttg ttttttgtttt gagaagtatg tatggtacat    7920
tctttgctgg gatggattat tgatactttc ttagccgccg tggcgtaaat gtaaccattt    7980
gctgggtttt agggatggag tcagtgaaag tcagtttacc caggtcatca acattgagct    8040
ggatcagatc atcgaggtaa tacatttgtt tgattcgtcc tttgcacatt tgcttgctta    8100
gttcaggaac gaattgcaag gtaacacatc cttgtaatta atgcaggcat gtaagtttct    8160
ggatgagaag tggtcacccca agttcactgt gattgttgct caaaagaacc accacaccaa    8220
gttctttcag acggcatcac cagacaatgt tcttcctggt aatatgttta ttttttgtcat    8280 actaaaggga gtgtggtgag atgcggtgac aataataaat gtgtttgttt gttacgcagg    8340
aactgtggtg gatagtaaag tttgccatcc taagaacttc gacttctaca tgtgtgcaca    8400
tgctgggatg attgtgagtt gatctcagaa ttgagcaaaa agatgctgct gtcttgttct    8460
tgtctctgaa tcctagatgg ttcttcgtct cagggaacaa caaggccgac ccactatcat    8520
gttctgcacg acgagatagg tttcagtgcc gacgagatgc aggagtttgt tcattcgctc    8580
tcttacgtgt aagtagtagt agtaaaatgc tgttttggct gtgtgtgtgt gtgtgtgttt    8640
tgtgcttacg ctgcgtgtcc tgctgtgcag gtaccagagg agcacgacag ccatctcagt    8700
gggtaggccg cttgaatcta aagccatctt gtgcagcaca gggacagcag gttgattttt    8760
ttctagtgtc tgttttttgtg tttgcagttg ctccagtgtg ctacgcccac ctcgctgcag    8820
cccaggtgag cacgttcctg agattggagg agatgtcaga cgcgtcctcc agccagggag    8880
gagggcatac ctcggctggc agtgctcctg tgccggagct gcctcgcctg catgacaaag    8940
tcaggagctc catgttcttc tgctagctga tgtgcgtgcg catcaggatc gagctccatg    9000
ttttgtgtta gtaaggccta gttagtaagg ctgtagaaag aatgtttaat gtttgcatgc    9060
taaagtccaa acaatcaaaa ccactactat atctaccaga gcactgatcg atcaaacaac    9120
aagagtcagc atcaatcaat caaaaccacc actattctat ctaccgatca atctactcta    9180
tacctgaagc actcactcgc tcgcaaacaa ccaagggatc atggatcctt gagtagctcc    9240
```

```
attgtccagt ccctgacctt gacgaagcat ttcatggaca gcctctcgta cgccatctcg    9300
tacatccgga ggttcatgta ggcgaagctc aagtaggtgg cgatgcactc ttggtgcctg    9360
tggtacagcg ccgggatggt cagagcggcc accacacttg cgtagcaggc ggtcgggaaa    9420
tctgtaacgc tgccgacgat ggacacgctc cacaggcaga ggaaggctct gtagaagagc    9480
agcgagtccc tgcccagagc gatgtcccgg aaagcgtccg aggcggcgtc cagagcagag    9540
cgcagcagcg ccgccgcctc gtccacggcc tgctgcggaa cgcgcagctc cgggacggga    9600
ggctgcggcc tgttcaggag gcgcgccgct ttggcccaca ggaagagcac ggtgaggagc    9660
aggagcagca cgttggaggc gagggacacc aaggtgtagc cgccgtacaa gagcagccag    9720
gaggagacgg tgcccgccag caggcaggcg ctcacgtcgg cgcggccccg gcgccacagc    9780
agcacgtccc agactgctgc agcaatccga tccgattccg atccagatat attagttagt    9840
agatccaatc tcgagcggcc aatccgtaat aataattggc tgagagaaaa ggtgggagag    9900
agtaccgaat cctccgacgg cacatgtccc ggcgccgccg ccgccgccgc caacaccaac    9960
accagcatcc accaccatcg tcgtagttaa tactaaggga agggaactag agaaggaagg   10020
gaggggccga tgcaacggaa gaaatggatg gaattcgacc aacagctagc tagagcgaag   10080
cagaacccaa tcccaatcaa aacccgagaa cgaacctgct tttactttcc caaccagacg   10140
gtggctggct tggaatccca ctatccctca ttccctctac caacagggca ccggcctggc   10200
ctccctcccc aatcatccaa ccaccacctt ttttttttctt cctttttgctg tgttttctta   10260 caaacttaaa tctactcgaa tattgattca agatattatg gagagtaatt gaatatttcg   10320
atgaatcacg tcatgtatat atttcttaat tacaaacttc tatcactatc aaataaagta   10380
aacataatgc tatttgcaat aatatatact atgtaaacat gactaaatca aaataaatgt   10440
ttaatttaat agttaccaag tttgcaagaa acatttcct tccaaagcac atatcatgat   10500
gctggcaatt tagttttatc agctataata atatcattga caacacattt tgtaagtcca   10560
cattctaaat aaattctgta cattataact aaaacattat atcatatcag cataaaaaat   10620
aaattaagta ttctatgttt ctataaaaca ataaaccatg cattgtacgg tgactgcgtc   10680
tagggaaaat tataccgcat gctagcaaaa cgtcctccag tatttcatta gacacattgg   10740
tgtcaaccta atatcctatt tgttgtcgtt ccaactaacc ccctcttata gtgctacaac   10800
actatcatct atgtgtgatg gttttactcg tgatacctca cttacaggtg aaaataagac   10860
cctcaaaaag gaggcgaatg agctcattca cgtcttaatt aaagcctaca gtagtgaggc   10920
tcacttgctt aaatgcttgg atagtcaaag attctaggta ttagactaag taactattct   10980
gttttgctac aaatgtatta gactaatgct gaagggcaaa tgccgaaggt aggtttcgac   11040
cagggcgcgc accaagactt tggtgatcat tgtgaacatg cttcggacga agctaattcc   11100
gaaggtccta tgggcgacga caaactaag                                    11129
```

<210> SEQ ID NO 8  
<211> LENGTH: 11129  
<212> TYPE: DNA  
<213> ORGANISM: Artificial Sequence  
<220> FEATURE:  
<223> OTHER INFORMATION: Description of Artificial Sequence: Synthetic  
      mutant polynucleotide  
<220> FEATURE:  
<221> NAME/KEY: modified_base  
<222> LOCATION: (3102)..(3111)  
<223> OTHER INFORMATION: a, c, t or g  
<220> FEATURE:  
<221> NAME/KEY: modified_base

```
<222> LOCATION: (6223)..(6232)
<223> OTHER INFORMATION: a, c, t or g
<220> FEATURE:
<221> NAME/KEY: modified_base
<222> LOCATION: (6310)..(6319)
<223> OTHER INFORMATION: a, c, t or g
<220> FEATURE:
<221> NAME/KEY: modified_base
<222> LOCATION: (6325)..(6326)
<223> OTHER INFORMATION: a, c, t or g

<400> SEQUENCE: 8
```

| | | | | | |
|---|---|---|---|---|---|
| tacacaagag | gagcgaagca | agtttcatcc | aacaggcttc | atcacggtga | aacgggtata | 60 |
| caacgtggct | tcggtataac | tcaaaggaag | tataacgaag | cacacttcat | caagcaggct | 120 |
| tcgtcataac | gaaacaatga | gatgcaagga | gaaggtgtta | ctcaagttat | taaatacaac | 180 |
| tgacgacatt | gcccttatga | catattgtaa | actctgtatg | taattattga | gggtataaat | 240 |
| gtaatagcgt | acgaacccct | gcgattgtct | ataaatagat | gaacattacc | ccgtactatt | 300 |
| cacgttggat | tgtaatcgct | ctcgcgtcaa | caccttcaaa | caagccgaag | atatcactgc | 360 |
| aatataaatt | ttgataatgt | ttatatattt | atcatggaat | aaatatatga | ctggatatca | 420 |
| cactcatgta | tttaaatcct | tattgatata | aatgatgagg | atgtgttatt | cacgaccttt | 480 |
| gtctgaagat | tattatatcc | gaaaggagat | atttttttcga | aggacgaatg | ttcttaacat | 540 |
| ttaataactg | tgttaccttg | ttcttgaaca | tgtgacaaac | attaggtttt | gagtatttca | 600 |
| attaatagtg | aaattaaatt | aaattttagt | tgtccaaaat | gacagacttc | gatatttgtt | 660 |
| ataattgttg | agttaaattt | taacagcatc | cataaacaag | taaacaacga | ctatgtgtgc | 720 |
| accagtgtct | cctgtatcaa | cggggtggtc | cgtctggagg | aggtaccgag | agataagtgc | 780 |
| tattatggac | gaagagggaa | ggggattcga | cgaaatggag | gcgttggcgt | tggcttctgt | 840 |
| gttttggaga | cgcacgcgac | agccaaactc | caaaacggat | acgagacagc | tcttggggct | 900 |
| gcgtaaacag | gtattagttt | tctgtccccg | tttaccgttc | ccgtgcgcag | acgccgtcac | 960 |
| gcgtactctt | cttgtctccg | tcgccgcgct | ctacggcggt | gctggcgtcc | gtgctgtact | 1020 |
| ccgcgccggc | agaggccgcg | cgcgcgtcgc | ccgcggacgg | cgccacgccg | ctccacctcg | 1080 |
| ccgcggccgt | gcacatcctc | ctcgccgcgg | gcgcgtccgt | ggacgcgcgc | gccttctcgg | 1140 |
| gcctccgcgc | cggggacctc | ctcctcccgc | gcgccaacga | ggccgccgcc | gccgcagacc | 1200 |
| gggcgctccg | cgtgctcctg | aagttccccg | cggcgtcact | gtcgtcctcg | cccaagaagt | 1260 |
| ccgcctcgcc | gccgccggcc | ccggaggcga | ggaaggagta | cccgcccgac | ctgacgctgc | 1320 |
| cggacctcaa | gagcgggctg | ttcagcaccg | acgagcaacg | gacgcacctt | acagctgtcc | 1380 |
| tagcactaat | tactcctaaa | ttcatcatac | accaaagttt | caattagtaa | aaggttttgg | 1440 |
| tattattttc | tttacaagac | taaaagcatc | cactcgtatt | tgccatggaa | atattgccaa | 1500 |
| aatggttacc | gaagaaccaa | tgaaaaatgg | cggtatccgt | ccacctgtaa | cttgtccaag | 1560 |
| gctcttccag | cagagtagtg | ccgccatgac | gattgacaga | gacacgagac | gaaacaagca | 1620 |
| gaaggtcccc | gcggcgtcac | tgtcgtcctc | gcccaagaag | tccgcctcgc | cgccgccggc | 1680 |
| cccggaggcg | aggaaggagt | acccgcccga | cctgacgctg | ccggacctca | agagcgggct | 1740 |
| gttcagcacc | gacgagttcc | gcatgtacag | cttcaaggtg | aagccctgct | cccgcaccta | 1800 |
| ctcgcacaac | tggaccgagt | gcccttcgtg | cacccgggcg | agaacgcgcg | cgccgtgac | 1860 |
| ccgcgcgtac | tcctacagct | gcgtgccctg | cccagagttc | cgcaagggcc | ggcgctgccg | 1920 |
| caagggcgac | ggctgcgagt | acgcgcacga | cgtcttcgag | tgctggctcc | accccggcgc | 1980 |

```
agtaccggac gcgcctctgc aaggacgagg tgggctgcgc gcgccgcatc tgcttcttcg   2040
cgcacaagcg cgaggagctc cgcgccgtca accccctccgc ggtgttcgtc ggcatgcaga   2100
tgcagcccac cgtgtcgccg ccgccgccca acggcctcgg cgacatgctc agcccggcgg   2160 cctggcc ctc ctccccgcg agcaggctca ataaggccgc gctcggcggc cgggacctgg   2220
accagtacca gcacatgttg ttcgacaagg tgtcgtcgcc gagggccagt tggagacaag   2280
aagagtacgc gtgacggaga tgcgacgag aaaaagggta cgcgtgacgg cgtctgcaca   2340
cgggaacggt aaacggggac aagaaactaa tacctgttta cgcagcccca agtgctgtct   2400
cgtatccgtt ttggagtttg gctgtcgcgt gcgtctccaa aacagagaag ccaacgccaa   2460
cgcctccatt tcgtcgaatc cccttccctc ttcgtccata atggcaatta tctcctcgtg   2520
ttcggtcccg ccgttcgaga gacgagctac gcatttaagc cggggaggtc ggagcagtga   2580
gtgggagtag ttcagggact gggagaggag aggaagcagg acctgggaga cctcgcctcg   2640
tccgtcctcc tgcctacttc cttgcttttg gtaagtgaaa gtgattgaag tggagatgcc   2700
tccaatctgc agtgctgttt cacgcgtaaa ccctggcccc ctcgccgctg aagcccccat   2760
tgttcctctt tcatttctta ccgctgatgc agcttatggt ttcctagggt tttcgagata   2820 tttggttttct tgcatccaga ggacgaagag cttcataggt gttttcgaga cattgtcctc   2880
acaatcgcat ccattctgca gtgctgtttc acgcgtaaac cctagcccct cgtcgctgga   2940
agcccacatg gttcctcttt catttcttac cgctgatgca gcttatgggt cctagggtt   3000 ttcgagacat ttggcttctt gcatccagag gacgaagagc tttcctaggg ttttcgagac   3060
attgtcctca caatcgcaga tttggttcga gacatttgtt tnnnnnnnnn ncgtcccgcg   3120
cttgagtcct tgtgatctgc acagcatgat gctgccacca aatgcatgca gttagacaag   3180
cttaatgttg catctgataa gactgtacaa cagattcgtg tgccaaatgt gtccttgcta   3240
ctcaaggagg tcatatggaa caagtaaaac gaaatttctg catcagcaat caggcacaag   3300
actgaatgac gtggttagtg ccaatgaggt ggggacttgg gaatgaatt agagttatag   3360 ctattcctat aattcatctc actacagagg ctctccatcc tactaggact gtacaacaga   3420
ttcgtgtgcc aaatgtgtcc ttgctactca aggaggtcat atggaacaag taaaacaaaa   3480
tttctgcatc agcaatcagg cacaagactg aatgacgtgg ttagtgccaa tgaggtggga   3540
acttgggaat ggaattagag ttatagctat tcctataatt catctcact   3600 acagaggctc tccatcctac tagaatttaa tctgataaag taggcagaaa catggaactt   3660
ataatgtcga agattgcatg tatagaatct aagtaacgga aagattcaac tttgtgatta   3720
tatgctgctg ttacatggta ttggtaaaac attctttcaa gtgctcattg tcttcccttg   3780
caaccaattc attgttgtcc ttgtttcctt gcaggtaggt gctgcttgtt ttatcttgaa   3840
atgggctctc atgatggcga ggatgaagag ttgccacccc cccctccggt gccaccagat   3900
gtgattccca ttaaagctga agatgctgtg ggtgaatcac cagcaaacca tatattaaag   3960
ccaaagagat tactgatgga caggcctggt ataggaagaa aagggcagcc gacccagctc   4020
tattcaaatc actttaaagt cgctgtgaag agtacagaag acgtcttctt tcactactat   4080
gtatgtctgc tgactgagtt catgatcctt tgttcaaaat atgtcattgt ctgtcccttg   4140
tttataacta atctttggct gatgtgatat tgttatttta tttgactagg taaacctgaa   4200
gtatgaggat gatcgacccg ttgatggtaa agggatcggc agaaaggtga ttgataaact   4260
gcagcagaca tatcgtgcag agctttctaa caaggacttt gtatatgatg gagaaaaagag   4320 cctgtttaca gttggtggtc ttccacaaaa aaagaatgag ttcaccgttg tcttggagga   4380
```

```
cgtatctact ggaaagttag ttttagtctt tgatctgctt tcttgttgtt tatgcttacc    4440
cagaatcagt aattgccatg ttttttgttt gtggttgtag gactgctgcc aatgggagcc    4500
ctggaggtaa tgacagtcct ggaggtggtg ataggaagag agtgaggagg ccataccaga    4560
cgaaaacttt caaagtggag ataaattttg cagcagaggt tcctatgagt gctattggtc    4620
aagtcattag aggcgaagaa tctgagaact ccctggaggc gcttcgtgtt cttgatatca    4680
tactgaggca gcattccgca gaacagtatg tagctatgca tcttgatgga tgattatagg    4740
tagatttgag gatcttctgc agttacgaca tgacaatttt tctcaatact gcagaggct     4800 gcctttggt taagcaatca ttttctaca acaacccttc atgctttgtt gacttgggtg       4860
gtggtgtgat gggttgtcgt ggatttcatt caagcttccg tggcacacag agtggacttt    4920
ccctcaatgt tggtgcgtgt tcgtcctgta tggctgtatt ggtgccatgt aactgcattg    4980
tctattctat aatcttacat ctttcatgat catgatagcc ttttttttg aaatccacag     5040 atgtctcaac aacaatgatc gtgaaacctg gccctgttat tgatttcctt ctttctaacc    5100
agaatgttaa tgatcctagc agaattgatt ggcaaaaggt aaatgccatc tttggatgaa    5160
acttctcgaa taaccatgct agtgcattga aatatctatt ttgatagaat gataacacaa    5220
ttttggggtg tgcatattca atacaggcca agcgtgctct caagggcttg aggattagaa    5280
ccactcctgc aaattcagaa ttcaagattt ttggtctcag cgagaggatc tgcaaagaac    5340
aaacgtgtgg acatgttttc ttaccgctct gtttattgtc atgcaagctt tactttacat    5400
ttttaaaaaa ttgtacccta gtgtgttaag cttgtttcag aagaattta tttaacaaat     5460 attgccttta ttgattttgt tctgattcca atgccaagct tgcttgatgg tgatatctgt    5520
gtgcttaatt gctttctcat tgacatatgc aattaggttt ccgctgaggc agagaaatgg    5580
tagcaacgga gattgtgata ccattgaaat aactgtctat gactactatg caaagaaagg    5640
aatcgatcta agtattctg gtgatttccc ctgtataaat acaggggaagg caaagcgccc     5700 aacatatttt ccaatcgagg tttgtttcag ttttgttagt tacatcctgt caaatctctg    5760
tttattaaat atatcttgca tctcatattc gatgggcagg cttggtgggg ctgtctcact    5820
gagtcactag gtcgtgggtt caaagcagcc tctccacatt tgtgggggg ggaaggcttg     5880 cttcggttta tcccttcctt agaccctagg tctgccccctt ttttttgcatc tcatttttt   5940 gtattgtgtt tctagctatg ctcgcttgtt ccgcttcaaa gatacaccaa agctttgtct    6000
acgctacaaa ggtcatccct tgtggagaag tctagacaga agcctgaaga aaggatgacc    6060
gttctaaatg atgtgagctg ttaccttgat tttagcatgc tgcgaccatt cataactgca    6120
tgggatttat ttctacgact gaattaatca acagcttatg attaccctaa atgctaggca    6180
ctgcaacgca gtaactacga ttctgacccc atgttgatgt gcnnnnnnnn nnaggttgag    6240
ggcatgtggt gtttcagttg ctccaaaatt tacccaagtt gaaggaagga tccttcaagc    6300
cccaaaggtn nnnnnnnng cttgnnagag aatcctaggg tgtttggatg gaattctagg    6360
atttaaagat ttttttccta tcctgattgt taatatctct atggatccaa acgctccctt    6420
agttgttttc tctctaaatg ttgtaccaag tcattatctc agtaaaatgc atctgactaa    6480
atctaatatc ttgtagctga aagccggcaa tggtgatgat atcttttcac gaaatggacg    6540
gtggaatttc actaataggg tcagcagctc aacatgtttc tttttttaacc ttctttttt    6600 ctttattagg aaggattttt ctgatgttta tttgccaata ctttgcccct tcagaagtt    6660 ttatgaaacc tgctctgtga ataagtgggc ggtcgttaat ttctctgcac gttgtgatgt    6720
```

-continued

```
tcggaatctt atccgtgacc tgatgaggaa tgcatctgca aagggaattg tatggtttag    6780
cttttcacat atcttctatt gtagcagttt tctgctgctg acgttttctt ctggcagcaa    6840
atggaggaac cttttgatgt gtttgaagag agtccctcta tgaggcgtgc acctgtgtca    6900
agaagggtgg atgatatgtt tgggcagata aaatcaaaac ttcctggagc tcctaggttc    6960
ctcttgtgcc ttctccctga gaggaaaaat tgtgaaatct atggttggtt tattttttgt    7020
taccactcca cataaatatc tcacatcttg caataattat accttttttgg tttcaaccag    7080 gtccttggaa gagaaagtgc ctggccgagt ttggtattgt cacacagtgt ctagctccat    7140
taagagtcaa tgatccgtac ctgcttaatt tgctgatgaa gatcaatgca aaggtttggg    7200
acatgatttt atctttcttt tgcactgtat tgttccctgg ttcatgatta tattatcctc    7260
tttcctctgt ttttaactag cttggtggtc tgaactcgtt gctgcaagtt gaagcatctt    7320
cgtcaatacc acatgtgtcg caagtaccca ccatcatctt aggtatggat gtttcacatg    7380
gtcatccagg acaagataga ccttcggttg cagcggtaag atgggtgtac ctttacttgt    7440
acaattcttc tgcccacatg aatctgagt ggttttgtaa aatatgtgaa atggatgtct    7500
gttaatctga tgtaaaccat accttctttc tttgtttagg tggttagttc tcgtcaatgg    7560
cctcttatct ctagatatag agcatcagtg cacacccaat ctgccagact agaaatgatg    7620
tcctcgttgt ttaagccgcg gggtactgat gatgatggcc tcatccggta agagatatct    7680
tcttagtatg ttgatgtatg gtaagcgtga tgacttttgg atgctaagtt tatcttcgta    7740
tttgggactt ccagggaatc actgatcgac ttctacacta gctctggaaa gcgaaaacca    7800
gaacacataa ttattttcag gtctgaagct ttgggggttat tgttagcttg tatcactaaa    7860 tcttttttgta gaaacaaatt ctttttttttg ttttttgtttt gagaagtatg tatggtacat    7920
tctttgctgg gatggattat tgatactttc ttagccgccg tggcgtaaat gtaaccattt    7980
gctgggtttt agggatggag tcagtgaaag tcagtttacc caggtcatca acattgagct    8040
ggatcagatc atcgaggtaa tacatttgtt tgattcgtcc tttgcacatt tgcttgctta    8100
gttcaggaac gaattgcaag gtaacacatc cttgtaatta atgcaggcat gtaagtttct    8160
ggatgagaag tggtcaccca agttcactgt gattgttgct caaaagaacc accacaccaa    8220
gttctttcag acggcatcac cagacaatgt tcttcctggt aatatgttta ttttttgtcat    8280 actaaaggga gtgtggtgag atgcggtgac aataataaat gtgtttgttt gttacgcagg    8340
aactgtggtg gatagtaaag tttgccatcc taagaacttc gacttctaca tgtgtgcaca    8400
tgctgggatg attgtgagtt gatctcagaa ttgagcaaaa agatgctgct gtcttgttct    8460
tgtctctgaa tcctagatgg ttcttcgtct cagggaacaa caaggccgac ccactatcat    8520
gttctgcacg acgagatagg tttcagtgcc gacgagatgc aggagtttgt tcattcgctc    8580
tcttacgtgt aagtagtagt agtaaaatgc tgttttggct gtgtgtgtgt gtgtgtgttt    8640
tgtgcttacg ctgcgtgtcc tgctgtgcag gtaccagagg agcacgacag ccatctcagt    8700
gggtaggccg cttgaatcta aagccatctt gtgcagcaca gggacagcag gttgattttt    8760
ttctagtgtc tgttttttgtg tttgcagttg ctccagtgtg ctacgcccac ctcgctgcag    8820
cccaggtgag cacgttcctg agattggagg agatgtcaga cgcgtcctcc agccaggag    8880 gagggcatac ctcggctggc agtgctcctg tgccggagct gcctcgcctg catgacaaag    8940
tcaggagctc catgttcttc tgctagctga tgtgcgtgcg catcaggatc gagctccatg    9000
ttttgtgtta gtaaggccta gttagtaagg ctgtagaaag aatgtttaat gtttgcatgc    9060
taaagtccaa acaatcaaaa ccactactat atctaccaga gcactgatcg atcaaacaac    9120
```

```
aagagtcagc atcaatcaat caaaaccacc actattctat ctaccgatca atctactcta    9180
tacctgaagc actcactcgc tcgcaaacaa ccaagggatc atggatcctt gagtagctcc    9240
attgtccagt ccctgacctt gacgaagcat tcatggaca gcctctcgta cgccatctcg     9300
tacatccgga ggttcatgta ggcgaagctc aagtaggtgg cgatgcactc ttggtgcctg    9360
tggtacagcg ccgggatggt cagagcggcc accacacttg cgtagcaggc ggtcgggaaa    9420
tctgtaacgc tgccgacgat ggacacgctc cacaggcaga ggaaggctct gtagaagagc    9480
agcgagtccc tgcccagagc gatgtcccgg aaagcgtccg aggcggcgtc cagagcagag    9540
cgcagcagcg ccgccgcctc gtccacggcc tgctgcggaa cgcgcagctc cgggacggga    9600
ggctgcggcc tgttcaggag gcgcgccgct ttggcccaca ggaagagcac ggtgaggagc    9660
aggagcagca cgttggaggc gagggacacc aaggtgtagc cgccgtacaa gagcagccag    9720
gaggagacgg tgcccgccag caggcaggcg ctcacgtcgg cgcggccccg gcgccacagc    9780
agcacgtccc agactgctgc agcaatccga tccgattccg atccagatat attagttagt    9840
agatccaatc tcgagcggcc aatccgtaat aataattggc tgagagaaaa ggtgggagag    9900
agtaccgaat cctccgacgg cacatgtccc ggcgccgccg ccgccgccgc caacaccaac    9960
accagcatcc accaccatcg tcgtagttaa tactaaggga agggaactag agaaggaagg   10020
gaggggccga tgcaacggaa gaaatggatg gaattcgacc aacagctagc tagagcgaag   10080
cagaacccaa tcccaatcaa aacccgagaa cgaacctgct tttactttcc caaccagacg   10140
gtggctggct tggaatccca ctatccctca ttccctctac caacagggca ccggcctggc   10200
ctccctcccc aatcatccaa ccaccacctt ttttttttctt cctttgctg tgttttctta    10260 caaacttaaa tctactcgaa tattgattca agatattatg gagagtaatt gaatatttcg   10320
atgaatcacg tcatgtatat atttcttaat tacaaacttc tatcactatc aaataaagta   10380
aacataatgc tatttgcaat aatatatact atgtaaacat gactaaatca aaataaatgt   10440
ttaatttaat agttaccaag tttgcaagaa aacatttcct tccaaagcac atatcatgat   10500
gctggcaatt tagtttttatc agctataata atatcattga caacacattt tgtaagtcca   10560
cattctaaat aaattctgta cattataact aaaacattat atcatatcag cataaaaaat   10620
aaattaagta ttctatgttt ctataaaaca ataaaccatg cattgtacgg tgactgcgtc   10680
tagggaaaat tataccgcat gctagcaaaa cgtcctccag tatttcatta gacacattgg   10740
tgtcaaccta atatcctatt tgttgtcgtt ccaactaacc ccctcttata gtgctacaac   10800
actatcatct atgtgtgatg gttttactcg tgatacctca cttacaggtg aaaataagac   10860
cctcaaaaag gaggcgaatg agctcattca cgtcttaatt aaagcctaca gtagtgaggc   10920
tcacttgctt aaatgcttgg atagtcaaag attctaggta ttagactaag taactattct   10980
gttttgctac aaatgtatta gactaatgct gaagggcaaa tgccgaaggt aggtttcgac   11040
cagggcgcgc accaagactt tggtgatcat tgtgaacatg cttcggacga agctaattcc   11100
gaaggtccta tgggcgacga caaactaag                                     11129
```

<210> SEQ ID NO 9
<211> LENGTH: 11120
<212> TYPE: DNA
<213> ORGANISM: Artificial Sequence
<220> FEATURE:
<223> OTHER INFORMATION: Description of Artificial Sequence: Synthetic mutant polynucleotide
<220> FEATURE:
<221> NAME/KEY: modified_base

```
<222> LOCATION: (3102)..(3102)
<223> OTHER INFORMATION: a, c, t or g
<220> FEATURE:
<221> NAME/KEY: modified_base
<222> LOCATION: (6214)..(6223)
<223> OTHER INFORMATION: a, c, t or g
<220> FEATURE:
<221> NAME/KEY: modified_base
<222> LOCATION: (6301)..(6310)
<223> OTHER INFORMATION: a, c, t or g
<220> FEATURE:
<221> NAME/KEY: modified_base
<222> LOCATION: (6316)..(6317)
<223> OTHER INFORMATION: a, c, t or g

<400> SEQUENCE: 9
tacacaagag gagcgaagca agtttcatcc aacaggcttc atcacggtga acgggtata      60 caacgtggct tcggtataac tcaaaggaag tataacgaag cacacttcat caagcaggct    120
tcgtcataac gaaacaatga gatgcaagga gaaggtgtta ctcaagttat taaatacaac    180
tgacgacatt gcccttatga catattgtaa actctgtatg taattattga gggtataaat    240
gtaatagcgt acgaacccct tgcgattgtct ataaatagat gaacattacc ccgtactatt   300
cacgttggat tgtaatcgct ctcgcgtcaa caccttcaaa caagccgaag atatcactgc    360
aatataaatt ttgataatgt ttatatattt atcatggaat aaatatatga ctggatatca    420
cactcatgta tttaaatcct tattgatata aatgatgagg atgtgttatt cacgaccttt    480
gtctgaagat tattatatcc gaaaggagat atttttttcga aggacgaatg ttcttaacat   540
ttaataactg tgttaccttg ttcttgaaca tgtgacaaac attaggtttt gagtatttca    600
attaatagtg aaattaaatt aaattttagt tgtccaaaat gacagacttc gatatttgtt    660
ataattgttg agttaaattt taacagcatc cataaacaag taaacaacga ctatgtgtgc    720
accagtgtct cctgtatcaa cggggtggtc cgtctggagg aggtaccgag gtcccgccgt    780
tcgagagacg agctacgcat ttaagccggg gaggtcggag cagtgagtgg gagtagttca    840
gggactggga gaggagagga agcaggacct gggagacctc gcctcgtccg tcctcctgcc    900
tacttccttg ctttttggtaa gtgaaagtga ttgaagtgga gatgcctcca atctgcagtg   960
ctgtttcacg cgtaaacctc ggccccctcg ccgctggaag ccccattgtt cctctttcat   1020
ttcttaccgc tgatgcagct tatggttttc tagggttttc gagatatttg gtttcttgca   1080
tccagaggac gaagagcttt catagggttt tcgagacatt gtcctcacaa tcgcatccat   1140
tctgcagtgc tgtttcacgc gtaaacccta gcccctcgtc gctggaagcc cacatggttc   1200
ctctttcatt tcttaccgct gatgcagctt atgggttcct agggttttcg agacatttgg   1260
cttcttgcat ccagaggacg aagagctttc ctagggtttt cgagacattg tcctcacaat   1320
cgcagatttg gttcgagaca tttgtttgag ataagtgcta ttatgacga agagggaagg    1380 ggattcgacg aaatggaggc gttggcgttg gcttctgtgt tttggagacg cacgcgacag   1440
ccaaactcca aaacggatac gagacagctc ttggggctgc gtaaacaggt attagttttc   1500
tgtccccgtt taccgttccc gtgcgcagac gccgtcacgc gtactcttct tgtctccgtc   1560
gccgcgctct acggcggtgc tggcgtccgt gctgtactcc gcgccggcag aggccgcgcg   1620
cgcgtcgccc gcgacggcg ccacgccgct ccacctcgcc gcggccgtgc acatcctcct   1680
cgccgcgggc gcgtccgtgg acgcgcgcgc cttctcgggc ctccgcgccg gggacctcct   1740
cctcccgcgc gccaacgagg ccgccgccgc cgcagaccgg gcgctccgcg tgctcctgaa   1800
gttccccgcg gcgtcactgt cgtcctcgcc caagaagtcc gcctcgccgc cgccggcccc   1860
```

```
ggaggcgagg aaggagtacc cgcccgacct gacgctgccg gacctcaaga gcgggctgtt      1920
cagcaccgac gagcaacgga cgcaccttac agctgtccta gcactaatta ctcctaaatt      1980
catcatacac caaagtttca attagtaaaa ggttttggta ttattttctt tacaagacta      2040
aaagcatcca ctcgtatttg ccatggaaat attgccaaaa tggttaccga agaaccaatg      2100
aaaaatggcg gtatccgtcc acctgtaact tgtccaaggc tcttccagca gagtagtgcc      2160
gccatgacga ttgacagaga cacgagacga aacaagcaga aggtcccgc ggcgtcactg       2220 tcgtcctcgc ccaagaagtc cgcctcgccg ccgccggccc cggaggcgag aaggagtac       2280 ccgcccgacc tgacgctgcc ggacctcaag agcgggctgt tcagcaccga cgagttccgc      2340
atgtacagct tcaaggtgaa gccctgctcc cgcacctact cgcacaactg gaccgagtgc      2400
ccttcgtgca cccgggcgag aacgcgcggc gccgtgaccc gcgcgtactc ctacagctgc      2460
gtgccctgcc ccgagttccg caagggccgg cgctgccgca agggcgacgg ctgcgagtac      2520
gcgcacgacg tcttcgagtg ctggctccac cccggcgcag taccggacgc gcctctgcaa      2580
ggacgaggtg ggctgcgcgc gccgcatctg cttcttcgcg cacaagcgcg aggagctccg      2640
cgccgtcaac ccctccgcgg tgttcgtcgg catgcagatg cagcccaccg tgtcgccgcc      2700
gccgcccaac ggcctcggcg acatgctcag cccggcggcc tggccctcct ccccccgcgag    2760 caggctcaat aaggccgcgc tcggcggccg ggacctggac cagtaccagc acatgttgtt      2820
cgacaaggtg tcgtcgccga gggccagttg agacaagaa gagtacgcgt gacggagatg       2880
cgacggagaa aaagggtacg cgtgacggcg tctgcacacg ggaacggtaa acggggacaa      2940
gaaactaata cctgtttacg cagccccaag tgctgtctcg tatccgtttt ggagtttggc      3000
tgtcgcgtgc gtctccaaaa cagagaagcc aacgccaacg cctccatttc gtcgaatccc      3060
cttccctctt cgtccataat ggcaattatc tcctcgtgtt cncgtcccgc gcttgagtcc      3120
ttgtgatctg cacagcatga tgctgccacc aaatgcatgc agttagacaa gcttaatgtt      3180
gcatctgata agactgtaca acagattcgt gtgccaaatg tgtccttgct actcaaggag      3240
gtcatatgga acaagtaaaa cgaaatttct gcatcagcaa tcaggcacaa gactgaatga      3300
cgtggttagt gccaatgagg tggggacttg ggaatggaat tagagttata gctattccta      3360
taattcatct cactacagag gctctccatc ctactaggac tgtacaacag attcgtgtgc      3420
caaatgtgtc cttgctactc aaggaggtca tatggaacaa gtaaaacaaa atttctgcat      3480
cagcaatcag gcacaagact gaatgacgtg gttagtgcca atgaggtggg aacttgggaa      3540
tggaattaga gttatagcta ttctatagct attcctataa ttcatctcac tacagaggct      3600
ctccatccta ctagaattta atctgataaa gtaggcagaa acatggaact tataatgtcg      3660
aagattgcat gtatagaatc taagtaacgg aaagattcaa cttttgtgatt atatgctgct     3720 gttacatggt attggtaaaa cattctttca agtgctcatt gtcttccctt gcaaccaatt      3780
cattgttgtc cttgttttcct tgcaggtagg tgctgcttgt tttatcttga atgggctct      3840 catgatggcg aggatgaaga gttgccaccc ccccctccgg tgccaccaga tgtgattccc      3900
attaaagctg aagatgctgt gggtgaatca ccagcaaacc atatattaaa gccaaagaga      3960
ttactgatgg acaggcctgg tataggaaga aaagggcagc cgacccagct ctattcaaat      4020
cactttaaag tcgctgtgaa gagtacagaa gacgtcttct ttcactacta tgtatgtctg      4080
ctgactgagt tcatgatcct ttgttcaaaa tatgtcattg tctgtccctt gtttataact      4140
aatctttggc tgatgtgata ttgttatttt atttgactag gtaaacctga agtatgagga      4200
tgatcgaccc gttgatggta aagggatcgg cagaaaggtg attgataaac tgcagcagac      4260
```

```
atatcgtgca gagctttcta acaaggactt tgtatatgat ggagaaaaga gcctgtttac    4320
agttggtggt cttccacaaa aaagaatga gttcaccgtt gtcttggagg acgtatctac    4380
tggaaagtta gttttagtct ttgatctgct ttcttgttgt ttatgcttac ccagaatcag    4440
taattgccat gttttttgtt tgtggttgta ggactgctgc caatgggagc cctggaggta    4500
atgacagtcc tggaggtggt gataggaaga gagtgaggag gccataccag acgaaaactt    4560
tcaaagtgga gataaatttt gcagcagagg ttcctatgag tgctattggt caagtcatta    4620
gaggcgaaga atctgagaac tccctggagg cgcttcgtgt tcttgatatc atactgaggc    4680
agcattccgc agaacagtat gtagctatgc atcttgatgg atgattatag gtagatttga    4740
ggatcttctg cagttacgac atgacaattt ttctcaatac ttgcagaggc tgccttttgg    4800
ttaagcaatc attttctac aacaaccctt catgctttgt tgacttgggt ggtggtgtga    4860
tgggttgtcg tggatttcat tcaagcttcc gtggcacaca gagtggactt ccctcaatg    4920 ttggtgcgtg ttcgtcctgt atggctgtat tggtgccatg taactgcatt gtctattcta    4980
taatcttaca tctttcatga tcatgatagc cttttttttt gaaatccaca gatgtctcaa    5040
caacaatgat cgtgaaacct ggccctgtta ttgattttct tctttctaac cagaatgtta    5100
atgatcctag cagaattgat tggcaaaagg taaatgccat ctttggatga aacttctcga    5160
ataaccatgc tagtgcattg aaatatctat tttgatagaa tgataacaca attttggggt    5220
gtgcatattc aatacaggcc aagcgtgctc tcaagggctt gaggattaga accactcctg    5280
caaattcaga attcaagatt tttggtctca gcgagaggat ctgcaaagaa caaacgtgtg    5340
gacatgtttt cttaccgctc tgtttattgt catgcaagct ttactttaca ttttttaaaaa   5400 attgtacct agtgtgttaa gcttgtttca gaagaatttt atttaacaaa tattgccttt    5460
attgattttg ttctgattcc aatgccaagc ttgcttgatg gtgatatctg tgtgcttaat    5520
tgctttctca ttgacatatg caattaggtt tccgctgagg cagagaaatg gtagcaacgg    5580
agattgtgat accattgaaa taactgtcta tgactactat gcaaagaaag gaatcgatct    5640
aaagtattct ggtgatttcc cctgtataaa tacagggaag gcaaagcgcc caacatattt    5700
tccaatcgag gtttgtttca gttttgttag ttacatcctg tcaaatctct gtttattaaa    5760
tatatcttgc atctcatatt cgatgggcag gcttggtggg gctgtctcac tgagtcacta    5820
ggtcgtgggt tcaaagcagc ctctccacat ttgtgggggg gggaaggctt gcttcggttt    5880
atcccttcct tagaccctag gtctgccccct ttttttgcat ctcattttt tgtattgtgt    5940 ttctagctat gctcgcttgt tccgcttcaa agatacacca aagctttgtc tacgctacaa    6000
aggtcatccc ttgtggagaa gtctagacag aagcctgaag aaaggatgac cgttctaaat    6060
gatgtgagct gttaccttga ttttagcatg ctgcgaccat tcataactgc atgggattta    6120
tttctacgac tgaattaatc aacagcttat gattacccta aatgctaggc actgcaacgc    6180
agtaactacg attctgaccc catgttgatg tgcnnnnnnn nnnaggttga gggcatgtgg    6240
tgtttcagtt gctccaaaat ttacccaagt tgaaggaagg atccttcaag ccccaaaggt    6300
nnnnnnnnnn gcttgnnaga gaatcctagg gtgtttggat ggaattctag gatttaaaga    6360
tttttttcct atcctgattg ttaatatctc tatggatcca aacgctccct tagttgtttt    6420
ctctctaaat gttgtaccaa gtcattatct cagtaaaatg catctgacta aatctaatat    6480
cttgtagctg aaagccggca atggtgatga tatcttttca cgaaatggac ggtggaattt    6540
cactaatagg gtcagcagct caacatgttt cttttttaac cttcttttttt tctttattag    6600
```

-continued

```
gaaggattttt tctgatgttt atttgccaat actttgccCC tttcagaagt tttatgaaac    6660
ctgctctgtg aataagtggg cggtcgttaa tttctctgca cgttgtgatg ttcggaatct    6720
tatccgtgac ctgatgagga atgcatctgc aaagggaatt gtatggttta gcttttcaca    6780
tatcttctat tgtagcagtt ttctgctgct gacgttttct tctggcagca aatggaggaa    6840
ccttttgatg tgtttgaaga gagtccctct atgaggcgtg cacctgtgtc aagaagggtg    6900
gatgatatgt ttgggcagat aaaatcaaaa cttcctggag ctcctaggtt cctcttgtgc    6960
cttctccctg agaggaaaaa ttgtgaaatc tatggttggt ttattttttg ttaccactcc    7020
acataaatat ctcacatctt gcaataatta tacctttttg gtttcaacca ggtccttgga    7080
agagaaagtg cctggccgag tttggtattg tcacacagtg tctagctcca ttaagagtca    7140
atgatccgta cctgcttaat ttgctgatga agatcaatgc aaaggtttgg gacatgattt    7200
tatcttctt ttgcactgta ttgttccctg gttcatgatt atattatcct ctttcctctg    7260
ttttaacta gcttggtggt ctgaactcgt tgctgcaagt tgaagcatct tcgtcaatac    7320
cacatgtgtc gcaagtaccc accatcatct taggtatgga tgtttcacat ggtcatccag    7380
gacaagatag accttcggtt gcagcggtaa gatgggtgta cctttacttg tacaattctt    7440
ctgcccacat ggaatctgag tggttttgta aaatatgtga aatggatgtc tgttaatctg    7500
atgtaaacca tacctttctt ctttgtttag gtggttagtt ctcgtcaatg gcctcttatc    7560
tctagatata gagcatcagt gcacacccaa tctgccagac tagaaatgat gtcctcgttg    7620
tttaagccgc ggggtactga tgatgatggc ctcatccggt aagagatatc ttcttagtat    7680
gttgatgtat ggtaagcgtg atgacttttg gatgctaagt ttatcttcgt atttgggact    7740
tccagggaat cactgatcga cttctacact agctctggaa agcgaaaacc agaacacata    7800
attattttca ggtctgaagc tttggggtta ttgttagctt gtatcactaa atctttttgt    7860
agaaacaaat tctttttttt gttttgttt tgagaagtat gtatggtaca ttctttgctg    7920
ggatggatta ttgatacttt cttagccgcc gtggcgtaaa tgtaaccatt tgctgggttt    7980
tagggatgga gtcagtgaaa gtcagtttac ccaggtcatc aacattgagc tggatcagat    8040
catcgaggta atacatttgt ttgattcgtc ctttgcacat ttgcttgctt agttcaggaa    8100
cgaattgcaa ggtaacacat ccttgtaatt aatgcaggca tgtaagtttc tggatgagaa    8160
gtggtcaccc aagttcactg tgattgttgc tcaaaagaac caccacacca agttctttca    8220
gacggcatca ccagacaatg ttcttcctgg taatatgttt attttgtca tactaaaggg    8280
agtgtggtga gatgcggtga caataataaa tgtgtttgtt tgttacgcag gaactgtggt    8340
ggatagtaaa gtttgccatc ctaagaactt cgacttctac atgtgtgcac atgctgggat    8400
gattgtgagt tgatctcaga attgagcaaa aagatgctgc tgtcttgttc ttgtctctga    8460
atcctagatg gttcttcgtc tcagggaaca acaaggccga cccactatca tgttctgcac    8520
gacgagatag gtttcagtgc cgacgagatg caggagtttg ttcattcgct ctcttacgtg    8580
taagtagtag tagtaaaatg ctgttttggc tgtgtgtgtg tgtgtgtgtt ttgtgcttac    8640
gctgcgtgtc ctgctgtgca ggtaccagag gagcacgaca gccatctcag tgggtaggcc    8700
gcttgaatct aaagccatct tgtgcagcac agggacagca ggttgatttt tttcagtgt    8760
ctgttttgt gtttgcagtt gctccagtgt gctacgccca cctcgctgca gcccaggtga    8820
gcacgttcct gagattggag gagatgtcag acgcgtcctc cagccaggga ggagggcata    8880
cctcggctgg cagtgctcct gtgccggagc tgcctcgcct gcatgacaaa gtcaggagct    8940
ccatgttctt ctgctagctg atgtgcgtgc gcatcaggat cgagctccat gttttgtgtt    9000
```

```
agtaaggcct agttagtaag gctgtagaaa gaatgtttaa tgtttgcatg ctaaagtcca    9060
aacaatcaaa accactacta tatctaccag agcactgatc gatcaaacaa caagagtcag    9120
catcaatcaa tcaaaccac cactattcta tctaccgatc aatctactct atacctgaag     9180
cactcactcg ctcgcaaaca accaagggat catggatcct tgagtagctc cattgtccag    9240
tccctgacct tgacgaagca tttcatggac agcctctcgt acgccatctc gtacatccgg    9300
aggttcatgt aggcgaagct caagtaggtg gcgatgcact cttggtgcct gtggtacagc    9360
gccgggatgg tcagagcggc caccacactt gcgtagcagg cggtcgggaa atctgtaacg    9420
ctgccgacga tggacacgct ccacaggcag aggaaggctc tgtagaagag cagcgagtcc    9480
ctgcccagag cgatgtcccg gaaagcgtcc gaggcggcgt ccagagcaga gcgcagcagc    9540
gccgccgcct cgtccacggc ctgctgcgga acgcgcagct ccgggacggg aggctgcggc    9600
ctgttcagga ggcgcgccgc tttggcccac aggaagagca cggtgaggag caggagcagc    9660
acgttggagg cgagggacac caaggtgtag ccgccgtaca agagcagcca ggaggagacg    9720
gtgcccgcca gcaggcaggc gctcacgtcg gcgcggcccc ggcgccacag cagcacgtcc    9780
cagactgctg cagcaatccg atccgattcc gatccagata tattagttag tagatccaat    9840
ctcgagcggc caatccgtaa taataattgg ctgagagaaa aggtgggaga gagtaccgaa    9900
tcctccgacg gcacatgtcc cggcgccgcc gccgccgccg ccaacaccaa caccagcatc    9960
caccaccatc gtcgtagtta atactaaggg aagggaacta gagaaggaag ggaggggccg   10020
atgcaacgga agaaatggat ggaattcgac caacagctag ctagagcgaa gcagaaccca   10080
atcccaatca aaacccgaga acgaacctgc ttttactttc ccaaccagac ggtggctggc   10140
ttggaatccc actatccctc attccctcta ccaacagggc accggcctgg cctccctccc   10200
caatcatcca accaccacct ttttttttct tccttttgct gtgttttctt acaaacttaa   10260
atctactcga atattgattc aagatattat ggagagtaat tgaatatttc gatgaatcac   10320
gtcatgtata tatttcttaa ttacaaactt ctatcactat caaataaagt aaacataatg   10380
ctatttgcaa taatatatac tatgtaaaca tgactaaatc aaaataaatg tttaatttaa   10440
tagttaccaa gtttgcaaga aaacatttcc ttccaaagca catatcatga tgctggcaat   10500
ttagttttat cagctataat aatatcattg acaacacatt ttgtaagtcc acattctaaa   10560
taaattctgt acattataac taaaacatta tatcatatca gcataaaaaa taaattaagt   10620
attctatgtt tctataaaac aataaaccat gcattgtacg gtgactgcgt ctagggaaaa   10680
ttataccgca tgctagcaaa acgtcctcca gtatttcatt agacacattg gtgtcaacct   10740
aatatcctat ttgttgtcgt tccaactaac cccctcttat agtgctacaa cactatcatc   10800
tatgtgtgat ggttttactc gtgataccct acttacaggt gaaataaga ccctcaaaaa    10860 ggaggcgaat gagctcattc acgtcttaat taaagcctac agtagtgagg ctcacttgct   10920
taaatgcttg gatagtcaaa gattctaggt attagactaa gtaactattc tgttttgcta   10980
caaatgtatt agactaatgc tgaagggcaa atgccgaagg taggtttcga ccagggcgcg   11040
caccaagact ttggtgatca ttgtgaacat gcttcggacg aagctaattc cgaaggtcct   11100
atgggcgacg acaaactaag                                               11120
```

MEANS FOR INDUCING APOXIMIS IN CULTIVATED PLANTS HAVING SEXUAL REPRODUCTION AND USE THEREOF FOR THE PRODUCTION OF COMPLETELY OR PARTIALLY APOMICTIC PLANTS

This application is the U.S. national phase of International Application No. PCT/IB2010/054769, filed 21 Oct. 2010, which designated the U.S. and claims priority to France Application No. 09/05046, filed 21 Oct. 2010, the entire contents of each of which are hereby incorporated by reference.

FIELD OF THE INVENTION

The subject of the invention is means for regulating reproductive development in cultivated plants. More particularly, the subject of the invention is the development of plants which reproduce completely or partially by gametophytic apomixis, i.e. asexually by means of seeds.

BACKGROUND OF THE INVENTION

Gametophytic apomixis is a form of asexual reproduction through seeds. It exists in numerous angiosperms, and close to 400 apomictic species have been listed. However, no apomictic plants are found among the main cultivated cereals (corn, wheat or rice), but only in wild plants, a few cultivated fodder species, and certain fruit species. Apomixis is a genetically controlled mechanism. Apomictic plants develop female gametes without prior meiosis. The gametes thus formed contain a genome identical to that of the somatic tissue from which they are derived. The development of the embryo from these gametes takes place without fertilization by a male gamete, i.e. by parthenogenesis. The genome of the embryo thus formed is therefore strictly identical to that of its mother plant, without paternal contribution. Apomixis is therefore a mode of cloning through seeds which ensures that genotypes are perpetuated identically through the generations.

The use of apomixis in a controlled manner in cultivated species offers many potential applications. These applications relate to the propagation of unstable genotypes, the control of pollen contaminations, methods for improving plants, and methods for the commercial production of seeds.

None of these applications can be envisioned in the main cultivated species such as wheat, corn, rice and the like, on the basis of current technologies. No apomictic forms are in fact known in these various species, and no genetic system which makes it possible to induce apomixis in sexual plants is known.

Many laboratories have, over the past years, endeavored to develop apomictic plants, either by attempting to transfer the determinants of apomixis from wild plants to cultivated plants, or by inducing apomictic phenotypes in sexual plants by mutagenesis. Neither of these two approaches has produced an apomictic genotype in a species in which this mode of reproduction did not exist beforehand.

Results recently published in the journal Nature (Ravi, M., Marimuthu, M. P., and Siddiqi, I. (2008). Gamete formation without meiosis in *Arabidopsis*. Nature 451: 1121-1124.), show, in *Arabidopsis*, that the inactivation of a gene involved in meiosis, called DYAD, the function of which is to regulate chromatid cohesion during meiosis, makes it possible to produce approximately 0.1% of gametes which escape meiosis. The remainder of the gametes, and therefore 99.9% of the descendants, are sterile. It is even probable that the frequency of non-meiotic gametes is not significantly different, in these mutant plants, than that in sexual plants, and that these gametes in fact become apparent only because the mutation kills, moreover, all the gametes normally derived from sexuality.

Another recent study (Erfurth, I., Jolivet, S., Froger, N., Catrice, O., Novatchkova, M., and Mercier, R. (2009). Turning meiosis into mitosis. PLoS Biol. 7: e1000124), shows that it is possible, in *Arabidopsis*, to change meiotic division into mitotic division through the simultaneous activation of three genes involved in meiosis (osd1/Atspo11-1/Atrec8). The triple mutant produces functional diploid gametes. However, these gametes are fertilized, the descendants are not therefore apomictic, and it is not known whether this result is transposable to species other than *Arabidopsis*.

The work by the inventors in the field have shown that it is possible to induce a completely or partially apomictic phenotype in corn by manipulating the expression of particular genes. The seeds produced evade meiotic reproduction and are fertile. These results advantageously apply to other cultivated plants such as rice or wheat.

SUMMARY OF THE INVENTION

The invention is therefore directed toward the use of specific nucleotide sequences, the manipulation of which makes it possible to develop cultivated plants, such as corn, rice and wheat, which reproduce completely or partially by gametophytic apomixis.

The objective of the invention is also to provide a method for producing apomictic plants.

According to yet another aspect, the invention aims to use apomixis in sexually reproducing cultivated species, in a controlled manner, for developing numerous applications, as will be set out hereinafter.

The invention is thus directed toward the use of a gene of the Argonaute family, of a transcript of this gene or of the ORF thereof for producing partially or completely apomictic plants.

This involves more especially a gene of the Argonaute family encoding a protein of sequence SEQ ID No. 1.

More particularly, the invention is directed toward the use of a gene of the Argonaute family corresponding to the sequence SEQ ID No. 2 or of the transcript of such a gene corresponding to the sequence SEQ ID No. 3, or of the ORF of sequence SEQ ID No. 4.

In the use according to the invention, the gene defined above is inactivated by mutagenesis.

Such an inactivation allows the formation of gametes of apomeiotic origin. The plants of which the protein is inactivated reproduce apomeiotically.

The invention is also directed toward a method for inducing a completely or partially apomictic phenotype in cultivated species such as corn, rice or wheat, characterized in that it comprises the targeted inactivation, by means of a transposable element, for example of Mutator type, of a gene, of a transcript of this gene, or of the ORF thereof, as defined above, and the identification of the mutated locus.

The use of apomixis in a controlled manner in cultivated species offers numerous potential applications. They relate to the propagation of unstable genotypes, the control of pollen contaminations, methods for improving plants, and methods for the commercial production of seeds.

The first application relates to the clonal propagation, through seeds, of genetically unstable genotypes. This is in particular the case for all hybrid plants; these hybrid plants produce, through genetic mixing during meiosis and fertilization, descendants which are different than one another, and different from their mother plant. This is also the case for cultivated species which have levels of ploidy that are unstable in meiosis, such as triploid forms.

In certain cultivated species, in order to maintain a high level of genetic purity, it is necessary to rigorously control pollination, in order to avoid contamination with pollen derived from more or less distant neighboring fields, it being possible for the pollen to move over quite variable distances, depending on the species, the climatic conditions, or the dissemination factors such as insects. In the case of apomictic plants, however, the genome resulting from the male gametes does not contribute to the next generation. The use of apomictic plants would therefore make it possible to dispense with the risks of contamination. Apomixis is therefore a totally unique method for controlling genetic purity. It is also potentially an effective method for avoiding undesirable transgene flow in the case of the growing of genetically modified organisms.

Apomixis also offers new perspectives in terms of plant improvement. It would in fact make it possible to use, as a new variety, any genotype selected as advantageous, provided that it involves a genetically determined criterion, regardless of the genetic structure, since, provided that it is apomictic, it becomes genetically stable. It is therefore possible to envision developing varieties directly from hybrid, optionally interspecific, forms, while dispensing with the stabilization steps currently necessary, such as successive self-fertilization steps, or the production of double haploids. This method therefore allows a considerable amount of time to be saved, but also opens the door to the introduction of completely new genetic materials into selection programs, and in particular of genetic materials which, in sexual plants, induce strong sterility. This is the case, for example, for most interspecific crosses.

A very important application relates to the production of hybrid seeds. As it is carried out today, this involves the controlled large-scale hybridization of genetically stable parental ecotypes. These are generally homozygous lines, obtained by various methods (production of doubled haploids, self-fertilizations, etc.). One of the two parents is used as the male, the other as the female. Only the females produce the commercial seeds. The yield from the seed production parcels is generally low compared with the hybrids, for three reasons: (1) the male lines are necessary but use a large part of the space without producing seeds; (2) the parental lines generally have a much lower yield than the hybrids owing to inbreeding depression; (3) pollination control involves physical or genetic castration of the lines used as females, a process which leads to a considerable loss of yield. However, in the case of apomictic plants, it could be envisioned to produce the seeds directly from hybrids, and therefore with much higher yields, using 100% of the available area, without the need to control pollination, and without a castration step. The advantage of using apomixis for seed production is very significant in species such as corn, where hybrid forms are already produced, for reasons of reduced costs, but also in autogamous species, for instance wheat or rice, where large-scale controlled hybridizations are difficult. The production of a few apomictic hybrid plants would be sufficient to initiate the large-scale production of genetically stable, hybrid seeds.

The partially or completely apomictic plants or plant seeds of cultivated species such as corn, rice and wheat, characterized in that they comprise inactivated alleles of a gene as defined above, also fall within the field of the invention.

The plants or plant seeds of the invention are advantageously as obtained by inactivation of the gene by mutagenesis or according to the method as described above, in order to induce in the cultivated plants a completely or partially apomictic phenotype.

BRIEF DESCRIPTION OF THE DRAWINGS

Other features and advantages of the invention are given by way of illustration in the examples which follow, in which reference is made to FIGS. 1 to 5, which represent, respectively, FIGS. 1A to 1C, the results relating to identification of apomeiotic plants in corn by means of a genetic screen;

FIG. 5, the FNR4 expression profile.

DEFINITIONS

The term "gametophytic apomixis" refers to a form of asexual reproduction through seeds, in which the gametes produced in the female gametophytes have not undergone meiotic reduction, and therefore have the same ploidy and the same genetic makeup as the mother plant. Gametophytic apomixis involves two successive stages: apomeiosis and parthenogenesis.

"Apomeiosis" corresponds to the mechanisms via which apomictic plants evade meiosis.

"Parthenogenesis" corresponds to the development of embryos without fertilization and without paternal genetic contribution.

DETAILED DESCRIPTION OF THE INVENTION

Example 1

Identification of Apomeiotic Plants by Means of a Targeted Genetic Screen

Figure 1:
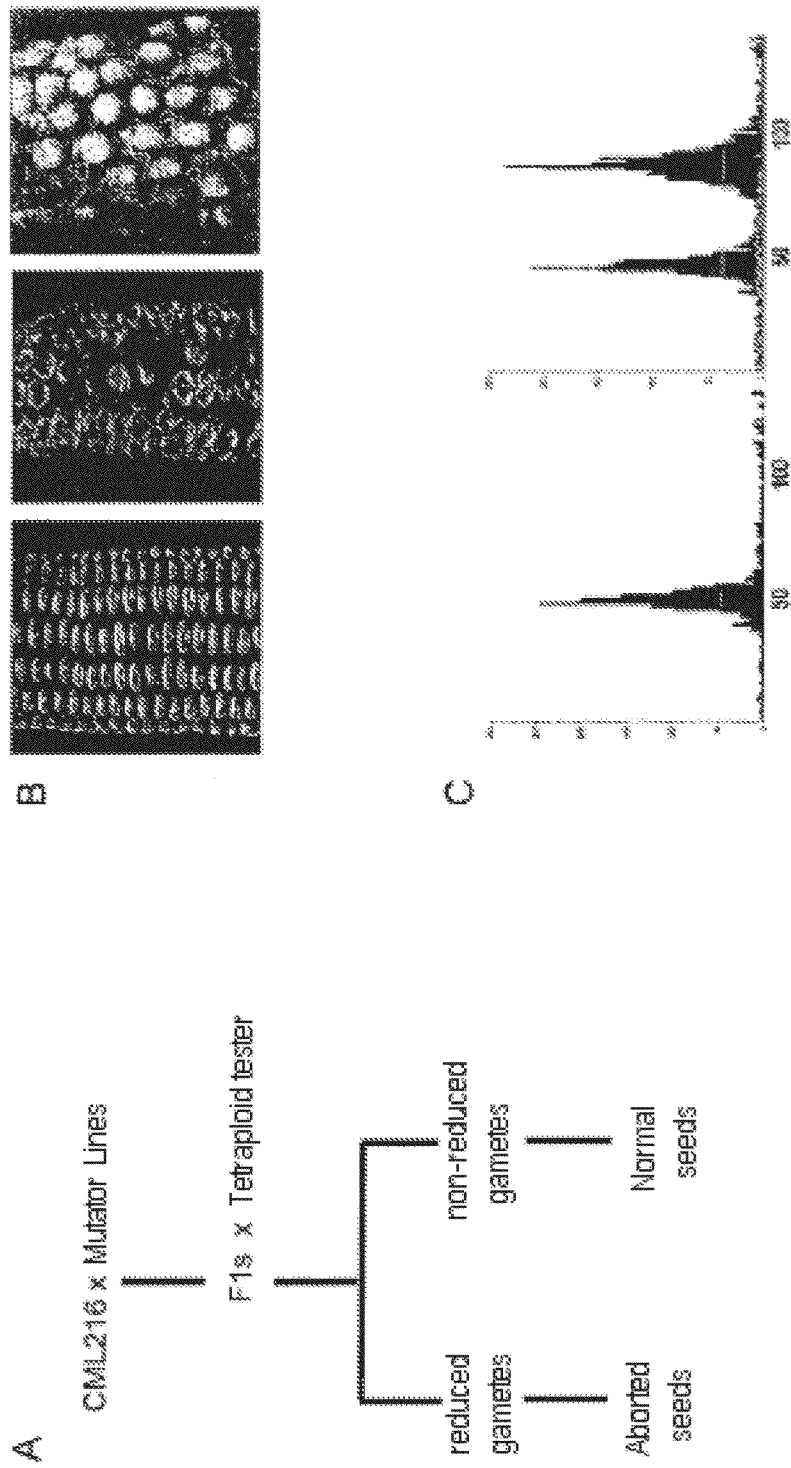

The results obtained are shown in FIGS. 1A to 1C:

In order to identify apomeiotic plants, a population of mutagenesis based on transposable elements of Mutator type, in a diploid genetic background, was constructed (FIG. 1A). The screen is based on the response of the albumen to a divergence in the respective ploidy levels of the male and female gametes.

When, in a wild-type corn plant, a diploid female is crossed with a tetraploid male, this results in an early abortion of the development of the albumen and therefore of the seed.

The results obtained are shown in FIG. 1B. When the gametes are at the same ploidy level (both haploids, or both diploids), the seed develops normally. In this screen, a tetraploid plant was used as male, and 15 000 mutagenized plants were used as females. The investigation related to the plants which, owing to the absence of meiotic reduction induced by mutation, produce gametes which are themselves diploid, and therefore in equilibrium with the genomic contribution of the diploid male gametes produced by the pollinator. In this screen, the vast majority of the plants exhibited the expected response, i.e. abortion of seed development. However, in the case of the fnr4 (Female Non Reduction 4) mutant, crossing with a tetraploid tester results in the formation of normally developed seeds. When analyzing these normally developed seeds, by means of a conventional flow cytometry analysis (FIG. 1C), it is verified that the embryo of these seeds exhibits a tetraploid genome, which is therefore the result of the fusion of two diploid gametes.

Figure 2:
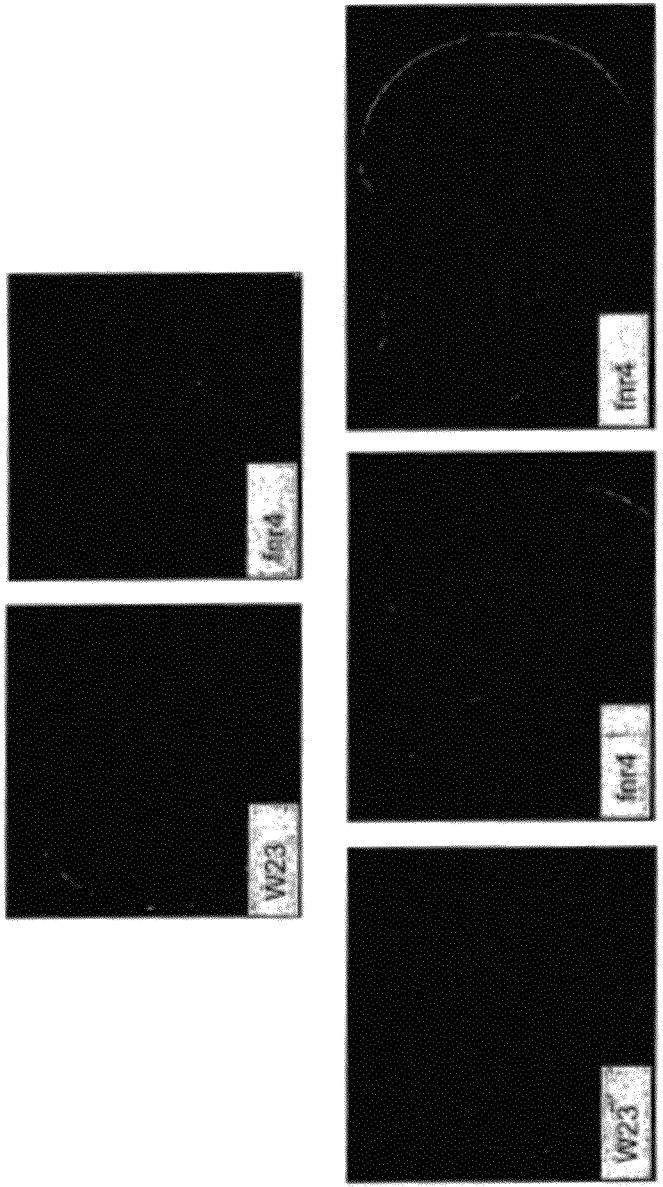
FIG. 2, the response of the cytological analysis of the FNR4 mutant.

The mutant plants therefore indeed produce apomeiotic gametes. The cytological analysis of the fnr4 mutant, reported on FIG. 2, indicates that the failure of meiosis is the result of defective chromosome condensation during meiosis and the disorganization, which results therefrom, of the mycotubule network constituting the meiotic spindle. The image is obtained by immunolocalization, firstly, of a specific antibody against beta-tubulin, visualized with a secondary antibody coupled to a fluorochrome (visible in the green range), and by labeling of the DNA with propidium iodide (visible in the red range). W23 is a wild-type line. The sequences of 3 mutant alleles, sequence SEQ ID Nos 7-9, comprising the Mutator insertion sequence, are given at the end of the description.

Example 2

Identification of the Modified Function in the Mutant Plants

Since the apomeiotic phenotype of the FNR4 mutant results from the random insertion of a transposable element of Mutator type into the genome, the sequence, which is known, of the Mutator elements was used for identifying the mutated locus by means of a conventional analysis of co-segregation between the phenotype and the sites of insertion of the various Mutator elements.

A candidate sequence could thus be identified and cloned. Analysis of three independent mutations in the same gene, all resulting from insertions of transposable elements, shows an identical phenotype. The locus identified therefore indeed corresponds to that responsible for the apomeiotic phenotype. Comparison of the sequence of the locus in the public database makes it possible to associate a biological function with this gene. It unambiguously appears to belong to a multigene family, comprising about twenty loci, all identified as encoding proteins of Argonaute type. These sequences of the gene (genomic, transcript and reading frame) correspond, respectively, to the sequences SEQ ID Nos 2, 3 and 4, and that of the corresponding protein to SEQ ID No. 1.

Figure 3:
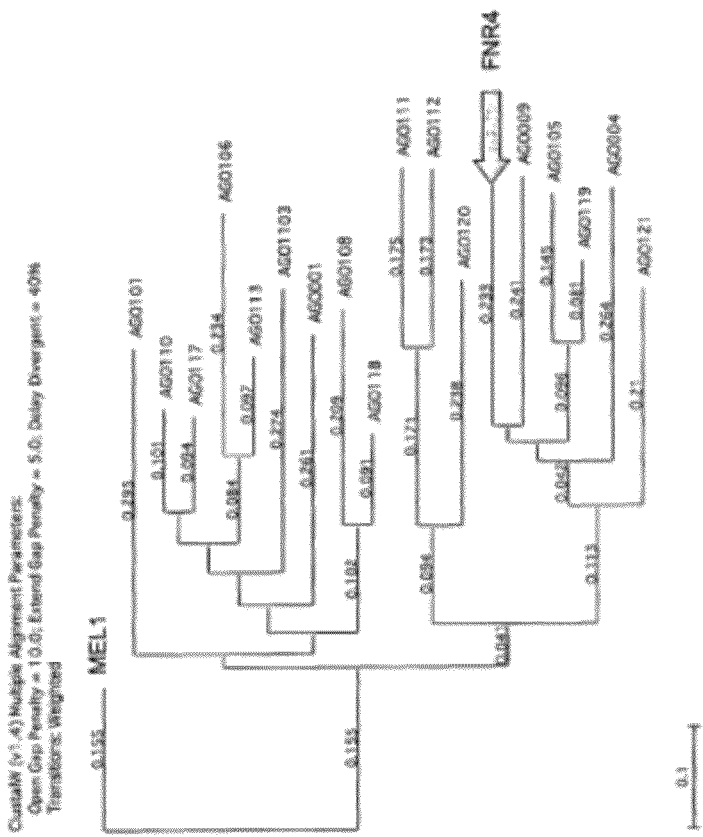
FIG. 3, the phylogenetic tree of the multigene family comprising the FNR4 mutant.

A phylogenetic tree comparing the protein sequence of FNR4 and that of the other known Argonautes in corn and in *Arabidopsis* is presented in FIG. 3. It includes the known members in *Arabidopsis* (AGO00X) and corn (AGO10X). The position, in this tree, of the MEL1 gene, which is another Argonaute gene, described in rice as being involved in the regulation of meiosis, is also indicated. The phenotype of a mel1 mutant is very different than fnr4, but it is important to note that it is, moreover, a clearly distinct Argonaute.

Figure 4:
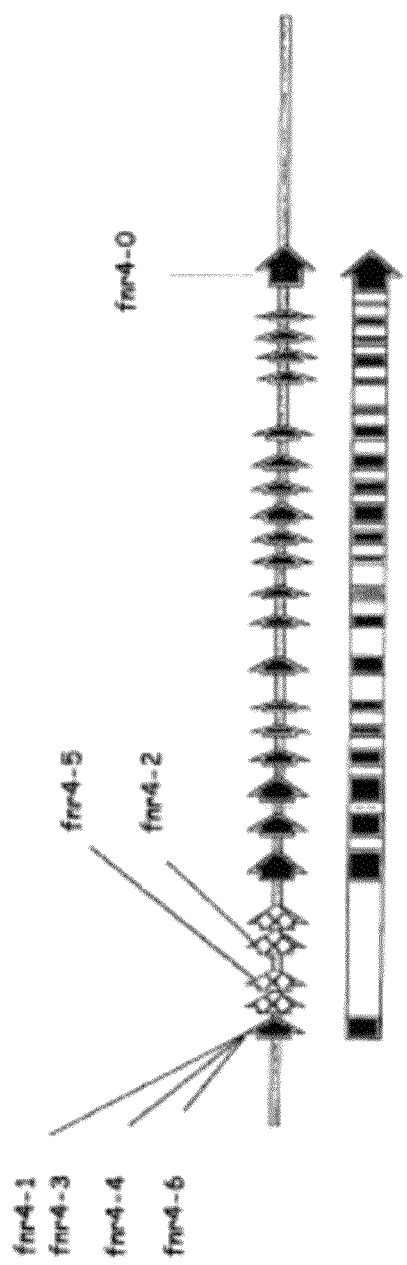
FIG. 4, the structure of the FNR4 gene and the sites for transposable-element insertions in the various alleles that are available.

FIG. 4 gives the structure of the FNR4 gene and the sites for transposable element insertions in the various alleles that are available.

Example 3

Expression Profile of the Gene and of the Protein in the Wild-Type Forms, the Apomeiotic Mutants and the Apomictic Plants The RT-PCR method was used to analyze the expression profile of the gene. The results show that the gene is expressed constitutively in all the tissues analyzed (leaves, mature pollen, pre-meiotic ovules, ovules during meiosis, ovules during gametogenesis, mature ovules before fertilization).

Using synthetic peptides designed on the basis of the sequence of the protein, antibodies specific for sequences SEQ ID No. 5 and SEQ ID No. 6, which make it possible to visualize by Western blotting the presence of the protein on extracts sampled at various stages of development, were generated. The detection of the antibody by immunodetection is shown in FIG. 5, A: Expression of the protein transcripts in corn. The specificity of the antibody used is validated through the use of mutant lines. B: tissue localization of the protein, limited to the basal part of the mature embryo sac; detection with a secondary antibody coupled to a fluorochrome (in green). DNA visualized in blue. The examination of FIG. 5A shows a band of expected size on the basis of the protein sequence, approximately 100 kD. The protein detected, unlike the RNA, is found only in the ovules, before and during meiosis. A residual presence is visible in the post-meiosis ovules, but no protein is detected in the other tissues of the plant.

The specificity of the antibody for the protein of the FNR4 locus was verified by testing, in parallel, the presence of the protein on ovules of the mutant plants. The signal of the antibody completely disappears in the mutants, thereby indicating excellent specificity. This shows, moreover, that the mutant plants indeed correspond to a loss of function.

Immunolocalization techniques were then used to study the localization of the protein at the tissue level. The results, shown in FIG. 5B, indicate that the protein is exclusively localized in the reproductive cells of the ovule. The gene is therefore expressed constitutively in the plant, but regulated post-transcriptionally, the corresponding protein having an expression profile exclusive to the reproductive cells.

The expression profile of the gene in apomictic ecotypes that are hybrid between corn and *Tripsacum* was also studied. These apomictic hybrid plants, obtained by crossing sexual corn plants and apomictic *Tripsacum* plants, exhibit the genome of the two species in the same cytoplasm. Using primers capable of detecting both the corn alleles and the *Tripsacum* alleles, the expression profile of the gene in the somatic and reproductive tissues of these plants is verified. It is noted that the transcripts detected by RT-PCR are absent from the apomictic forms.

The invention claimed is:

1. A method for producing a partially or completely apomictic cultivated cereal plant, comprising inactivating a gene of the Argonaute family comprising the sequence SEQ ID NO: 2, said gene encoding a protein comprising the sequence SEQ ID NO: 1, or of a transcript of said gene comprising the sequence SEQ ID NO: 3, or of an ORF of said gene comprising the sequence SEQ ID NO: 4.

2. The method as claimed in claim 1, wherein said gene is inactivated by mutagenesis.

3. A method for inducing a completely or partially apomictic phenotype in a cultivated cereal plant, the method comprising targeted inactivation, by means of a transposable element, of a gene of the Argonaute family comprising the sequence SEQ ID NO: 2, or of a transcript of said gene comprising the sequence SEQ ID NO: 3, or of an ORF of said gene comprising the sequence of SEQ ID NO: 4.

4. The method as claimed in claim 3, wherein the method is applied for at least one of propagation of unstable genotypes, control of pollen contamination, plant improvement, and commercial production of seeds.

5. A genetically modified, completely or partially apomictic cultivated cereal plant or plant seed, wherein said plant or seed comprises inactivated alleles of a gene of the Argonaute family of the sequence of SEQ ID NO: 2.

6. A genetically modified, completely or partially apomictic cultivated cereal plant or plant seed, obtained according to the method of claim 3.

7. The method of claim 3, wherein said plant is corn, rice or wheat.

8. The plant or plant seed of claim 5, wherein said plant is corn, rice or wheat.

9. The plant or plant seed of claim 6, wherein said plant is corn, rice or wheat.

* * * * *